US011065266B2

(12) United States Patent
Acevedo-Duncan et al.

(10) Patent No.: US 11,065,266 B2
(45) Date of Patent: Jul. 20, 2021

(54) METHOD OF TREATING MELANOMA USING AN INHIBITOR OF AN ATYPICAL PROTEIN KINASE C

(71) Applicants: UNIVERSITY OF SOUTH FLORIDA, Tampa, FL (US); UNIVERSITY OF FLORIDA RESEARCH FOUNDATION, INC., Gainesville, FL (US)

(72) Inventors: Mildred Enid Acevedo-Duncan, Plant City, FL (US); Wishrawana Sarathi Ratnayake, Tampa, FL (US); David A. Ostrov, Gainesville, FL (US)

(73) Assignees: UNIVERSITY OF SOUTH FLORIDA, Tampa, FL (US); UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 16/554,187

(22) Filed: Aug. 28, 2019

(65) Prior Publication Data
US 2020/0022994 A1    Jan. 23, 2020

Related U.S. Application Data

(62) Division of application No. 15/612,642, filed on Jun. 2, 2017, now Pat. No. 10,918,650.

(60) Provisional application No. 62/344,747, filed on Jun. 2, 2016, provisional application No. 62/453,751, filed on Feb. 2, 2017.

(51) Int. Cl.
| | |
|---|---|
| *A61K 31/675* | (2006.01) |
| *A61K 31/122* | (2006.01) |
| *A61K 31/185* | (2006.01) |
| *A61K 45/06* | (2006.01) |
| *A61K 31/255* | (2006.01) |
| *A61K 31/194* | (2006.01) |
| *C12Q 1/6886* | (2018.01) |
| *G01N 33/574* | (2006.01) |

(52) U.S. Cl.
CPC .......... *A61K 31/675* (2013.01); *A61K 31/122* (2013.01); *A61K 31/185* (2013.01); *A61K 31/194* (2013.01); *A61K 31/255* (2013.01); *A61K 45/06* (2013.01); *C12Q 1/6886* (2013.01); *C12Y 207/11013* (2013.01); *G01N 33/5743* (2013.01); *C12Q 2600/106* (2013.01); *C12Q 2600/158* (2013.01); *G01N 2333/91205* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 8,883,841 | B2 * | 11/2014 | Fang | A61K 31/404 514/415 |
| 8,889,672 | B2 * | 11/2014 | Antonetti | A61K 31/496 514/231.5 |
| 9,078,915 | B2 | 7/2015 | Acevedo-Duncan et al. | |
| 9,301,965 | B2 | 4/2016 | Acevedo-Duncan et al. | |
| 9,351,981 | B2 | 5/2016 | Acevedo-Duncan et al. | |
| 10,918,650 | B2 * | 2/2021 | Acevedo-Duncan | A61K 31/194 |
| 2008/0026088 | A1 | 1/2008 | Tripp et al. | |
| 2012/0028394 | A1 | 2/2012 | Lim | |
| 2018/0008564 | A1 | 1/2018 | Acevedo-Duncan | |

FOREIGN PATENT DOCUMENTS

WO    WO-2015/056180 A1    4/2015

OTHER PUBLICATIONS

Lens, M.B. et al., "Global perspectives of contemporary epidemiological trends of cutaneous malignant melanoma", Topical Review, *British Journal of Dermatology*, 2004, 150:179-185, 2004 British Association of Dermatologists.
Lee, J.A.H. et al., "Malignant Melanoma: Social Status and Outdoor Work", *Br. J. Cancer*, 1980, 41:757-763.
Pollock, P.M. et al., "A genome-based strategy uncovers frequent BRAF mutations in melanoma", *Cancer Cell*, Jul. 2002, pp. 5-7.
Cutler, R.E. et al., "Autoregulation of the Raf-1 serine/threonine kinase", *Proceedings of the National Academy of Sciences of the United States of America, Biochemistry*, Aug. 1998, 95(16):1-7, National Academy of Sciences.
Greene, M.H., "The Genetics of Heredity Melanoma and Nevi 1998 Update", *Cancer Supplement*, Dec. 1, 1999, 86(11):2464-2477, 1999 American Cancer Society.
Halachmi, S. et al., "Update on genetic events in the pathogenesis of melanoma", *Current Opinion in Oncology*, 2001, 13:129-136, 2001 Lippincott Williams & Wilkins, Inc.
Manning, G. et al., "The Protein Kinase Complement of the Human Genome", *Science*, Dec. 6, 2002, 298:1912-1934.
Kishimoto, A. et al., "Activation of Calcium and Phospholipid-dependent Protein Kinase by Diacylglycerol, Its Possible Relation to Phosphatidylinositol Turnover", *The Journal of Biological Chemistry*, 1980, 255(6):1-5.

(Continued)

*Primary Examiner* — My-Chau T. Tran
(74) *Attorney, Agent, or Firm* — Quarles & Brady LLP

(57) ABSTRACT

The invention pertains to a method of treating melanoma by administering to a subject in need thereof, a composition comprising a therapeutically effective amount of an inhibitor of PKC-ζ and/or PKC-ι. Non-limiting examples of an inhibitor of PKC-ζ and/or PKC-ι include ICA-1 and ACPD. The invention also provides PKC-ζ and/or PKC-ι as biomarkers for identifying a melanoma in a subject as likely to be responsive or non-responsive to a therapy using an inhibitor of PKC-ζ and/or PKC-ι. Accordingly, a method of identifying a subject having a melanoma as being responsive or non-responsive to a melanoma therapy with an inhibitor of PKC-ζ and/or PKC-ι based on the levels and/or activity of PKC-ζ and/or PKC-ι mRNA or protein in the melanoma cells from the subject are also provided.

9 Claims, 24 Drawing Sheets
(9 of 24 Drawing Sheet(s) Filed in Color)

(56) References Cited

OTHER PUBLICATIONS

Castagna, M. et al., "Direct Activation of Calcium-activated, Phospholipid-dependent Protein Kinase by Tumor-promoting Phorbol Esters", *The Journal of Biological Chemistry*, 1992, 257(19):1-6.
Wilson, C.H. et al., "Steatosis inhibits liver cell store-operated $Ca^{2+}$ entry and reduces ER $Ca^{2+}$ through a protein Kinase C-dependent mechanism", *Biochemical Journal*, 2015, 466:1-13, The Authors Journal Compilation, 2015 Biochemical Society.
Mellor, H. et al., "The extended protein kinase C superfamily", *Biochemical Journal*, 1998, 332:281-292.
Selzer, E. et al., "Protein kinase C isoforms in normal and transformed cells of the melanocytic lineage", *Melanoma Research*, 2002, 12:201-209, 2002 Lippincott Williams & Wilkins.
Regala, R.P. et al., "Atypical Protein Kinase Cι Plays a Critical Role in Human Lung Cancer Cell Growth and Tumorigenicity", *The Journal of Biological Chemistry*, 2005, 280(35):1-8, 2005 The American Society for Biochemistry and Molecular Biology, Inc.
Bandyopadhyay, G. et al., "PCK-ζ Mediates Insulin Effects on Glucose Transport in Cultured Preadipocyte-Derived Human Adipocytes", *The Journal of Clinical Endocrinology & Metabolism*, Feb. 2002, 87(2):716-723, 2002 The Endocrine Society.
Plant, P.J. et al., "A polarity complex of mPar-6 and atypical PKC binds, phosphorylates and regulates mammalian Lgl", *Nature Cell Biology*, pp. 1-8, 2003 Nature Publishing Group.
Murray, N.R. et al., "Atypical Protein Kinase Cι Protects Human Leukemia Cells against Drug-induced Apoptosis", *The Journal of Biological Chemistry*, 1997, 272(44):1-5, 1997 The American Society for Biochemistry and Molecular Biology, Inc.
Acevedo-Duncan, M. et al., "Human Glioma PKC-ι and PKC-ββII phosphorylate cyclin-dependent kinase activating kinase during the cell cycle", *Cell Proliferation*, 2002, 23-36, 2002 Blackwell Science Ltd.
Patel, R. et al., "Involvement of PKC-ι in glioma proliferation", *Cell Proliferation*, 2008, 41:122-135, VA Hospital, 2008 Blackwell Publishing Ltd.
Dissanayake, S.K. et at, "The Wnt5A/Protein Kinase C Pathway Mediates Motility in Melanoma Cells via the Inhibition of Metastasis Suppressors and Initiation of an Epithelial to Mesenchymal Transition", *The Journal of Biological Chemistry*, Jun. 8, 2007, 282(23):1-14, JBC Papers in Press.
Weeraratna, A.T. et al., "Wnt5a signaling directly affects cell motility and invasion of metastatic melanoma", *Cancer Cell*, Apr. 2002, 1:279-288, 2002 Cell Press.
So, T. et al., "Regulation of the PKCθ-NF-$_k$B axis in T lymphocytes by the tumor necrosis factor receptor family member OX40", Article 133, *Frontiers in Immunology*, May 28, 2012, 3:1-8.
Sun, S., "Non-canonical NF-$_k$B signaling pathway", *Cell Research*, 2011, 21(1):71-85, 2011 IBCB, SIBS, CAS.
Liu, N. et al., "MicroRNA-9 suppresses uveal melanoma cell migration and invasion through the NF-$_k$B1 pathway", *Oncology Reports*, 2012, 28:961-968.
Semenov, M.V. et al., "Snapshot: Noncanonical Wnt Signaling Pathways", *Cell*, Dec. 28, 2007, 131:1-2, 2007 Elsevier Inc.
O'Connell, MP. et al., "The orphan tyrosine kinase receptor, ROR2, mediates Wnt5A signaling in metastatic melanoma", *Oncogene*, 2010, 29:34-44, 2010 Macmillan Publishers Limited.
Vultur, A. et al., "MEK inhibition affects STAT3 signaling and invasion in human melanoma cell lines", *Oncogene*, 2014, 33:1850-1861, 2014 Macmillan Publishers Limited.

McKinsey, T.A. et al., "Small-molecule therapies for cardiac hypertrophy: moving beneath the cell surface", *Nature Reviews*, Aug. 2007, 6:617-635, 2007 Nature Publishing Group.
Murakoshi, H. et al., "Local, persistent activation of Rho GTPases during plasticity of single dendritic spines", *Nature*, Apr. 7, 2011, 472:1-7, 2011 Macmillan Publishers Limited.
Pillai, P. et al., "A novel PKC-ι inhibitor abrogates cell proliferation and induces apoptosis in neuroblastoma", *The International Journal of Biochemistry & Cell Biology*, 2011, 43:784-794, Elsevier Ltd.
Guertin, M.J. et al., "*Drosophila* Heat Shock System as a General Model to Investigate Transcriptional Regulation", *Cold Spring Harbor Symposia on Quantitative Biology*, 75:1-9, 2010 Cold Spring Harbor Laboratory Press.
Salamanca, H.H. et al., "An RNA aptamer perturbs heat shock transcription factor activity in *Drosophila melanogaster*", *Nucleic Acids Research*, 2011, 39(15):6729-6740, The Author(s) 2011, Oxford University Press.
Regala, R.P. et al., "Atypical Protein Kinase Cι Is an Oncogene in Human Non-Small Cell Lung Cancer", *Cancer Research*, Oct. 1, 2005, 65(19):1-8, 2005 American Association for Cancer Research.
"Melanoma Treatment-Health Professional Version", Web page <http://www.cancer.gov/types/skin/hp/melanoma-treatment-pdq>, 5 pages, Mar. 6, 2016, retrieved from Internet Archive Wayback Machine <https://web.archive.org/web/20160306105404/http://www.cancer.gov/types/skin/hp/melanoma-treatment-pdq> on Jul. 19, 2018.
"One Molecule, Multiple Cancers: The Devil is in the Details", Web Page <http://www.home.ccr.cancer.gov/connections/2011/Vol5_No1/clinic.asp>, 3 pages, Oct. 15, 2011, retrieved from Internet Archive Wayback Machine <https://web.archive.orq/web/20111015004903/https://home.ccr.cancer.gov/connections/2011/Vol5No1/clinic.asp>, on Jul. 19, 2018.
"Surveillance, Epidemiology, and End Results Program", Web Page <https://seer.cancer.gov/statistics/types/survival.html>, 1 page, Mar. 16, 2016, retrieved from Internet Archive Wayback Machine <https://web.archive.org/web/20160316160345/https://seer.cancer.gov/statistics/types/survival.html>, on Jul. 19, 2018.
Ratnayake, W. S. et al., "Two novel atypical PKC inhibitors; ACPD and DNDA effectively mitigate cell proliferation and epithelial to mesenchymal transition of metastatic melanoma while inducing apoptosis," *International Journal of Oncology*, 2017, 51:1370-1382.
Ratnayake W. S. et al., "Abstract 862: Atypical protein kinase c inhibitors can repress epithelial to mesenchymal transition (type III) in malignant melanoma," *Cancer Research*, Jul. 2017, p. 1, American Association for Cancer Research.
Anthonsen, M. W. et al., "Atypical λ/ιPKC Conveys 5-Lipoxygenase/Leukotriene $B_4$-mediated Cross-talk between Phospholipase $A_2$s Regulating NF-κB Activation in Response to Tumor Necrosis Factor-α and Interleukin-1β*," *The Journal of Biological Chemistry*, 2001, 276(38):35344-35351,The American Society for Biochemistry and Molecular Biology, Inc.
National Center for Biotechnology Information. PubChem Compound Database; CID=165388, https://pubchem.ncbi.nim.nih.gov/compound/165388 (accessed Apr. 11, 2018). (Year: 2018).
Atwood, S. X. et al., "GLI Activiation by atypical protein kinase C ι/λ regulates the growth of basal cell carcinomas," *Nature*, Feb. 28, 2013, 494:484-488, Macmillan Publishers Limited.
Faurschou, A. et al., "TNF-α stimulates Akt by a distinct aPKC-dependent pathway in premalignant keratinocytes," *Experimental Dermatology*, 2008, 17:992-997.
Huang, C. et al., "Inhibition of Atypical PKC Blocks Ultraviolet-Induced AP-1 Activation by Specifically Inhibiting ERKs Activation," *Molecular Carcinogenesis*, 2000, 27:65-75, Wiley-Liss, Inc.

* cited by examiner

A.
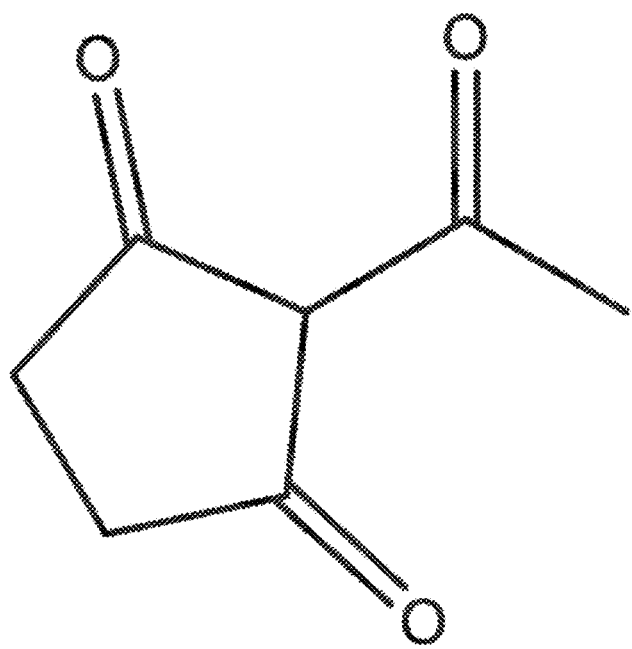
B.
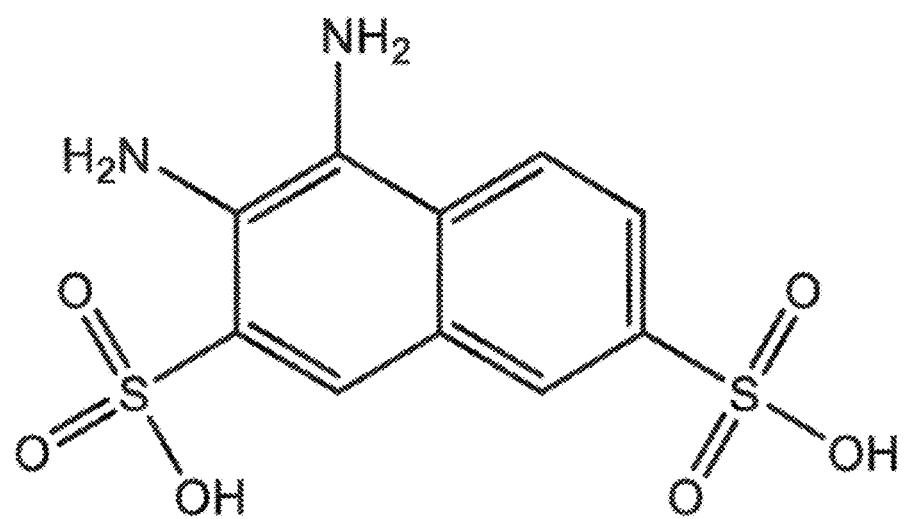
Figure 1A-B

A.
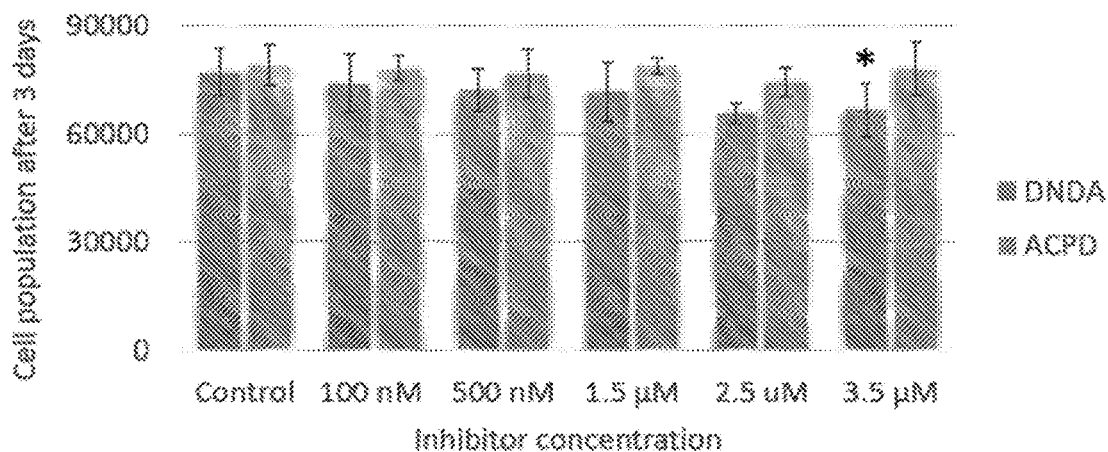
B.
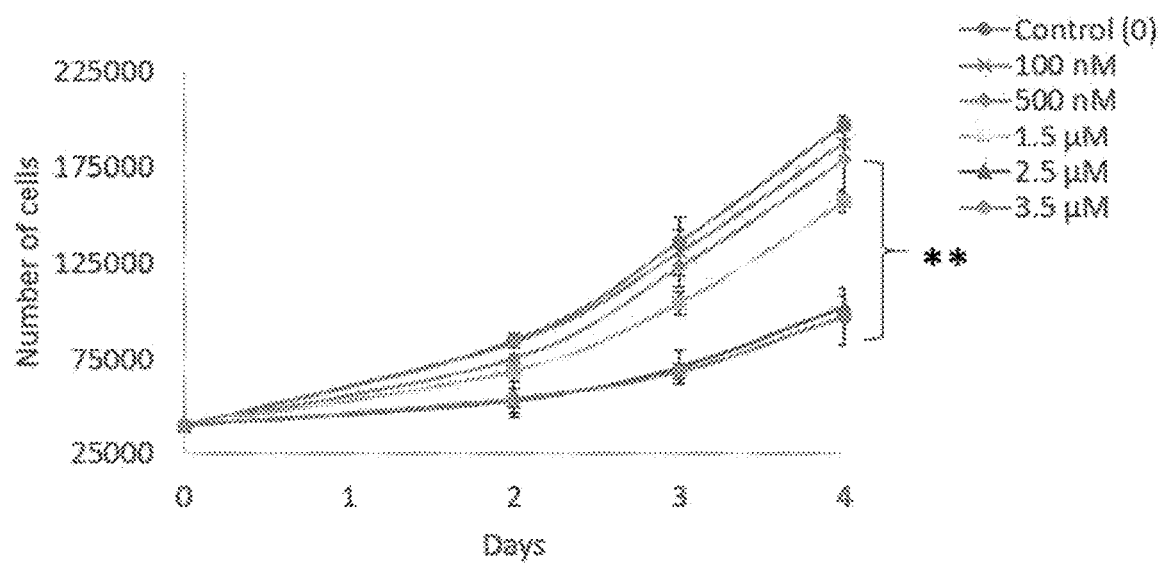
Figure 5A-B

C.
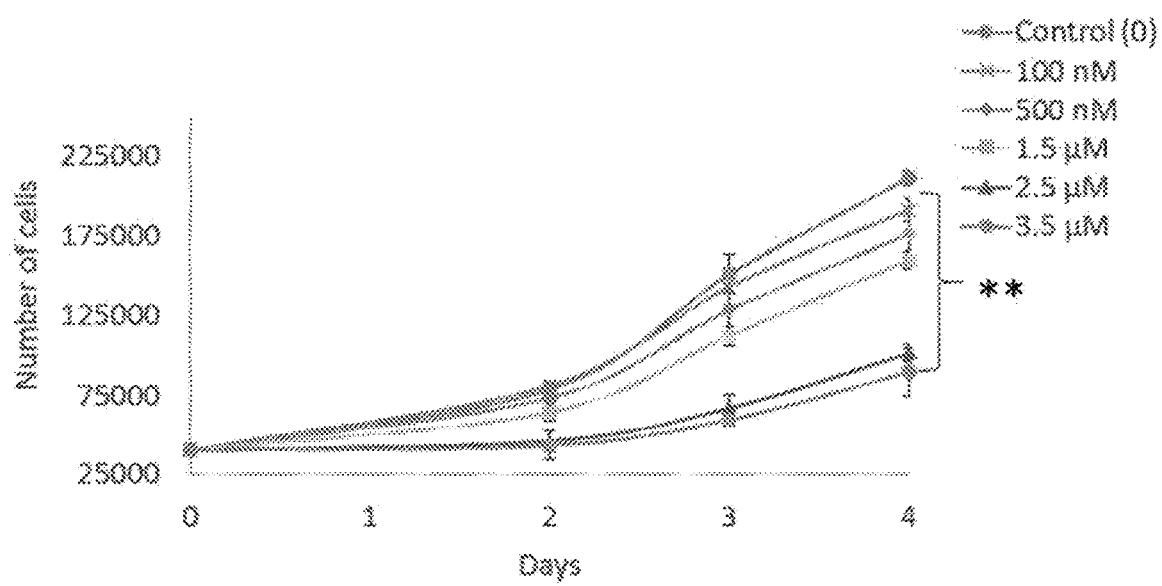
D.
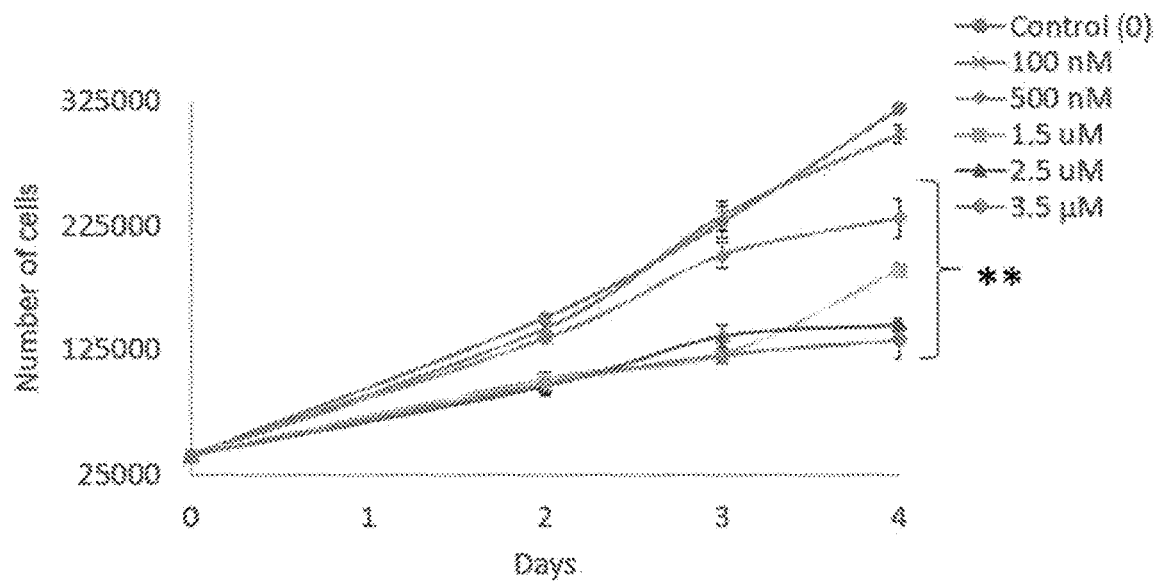
Figure 5C-D

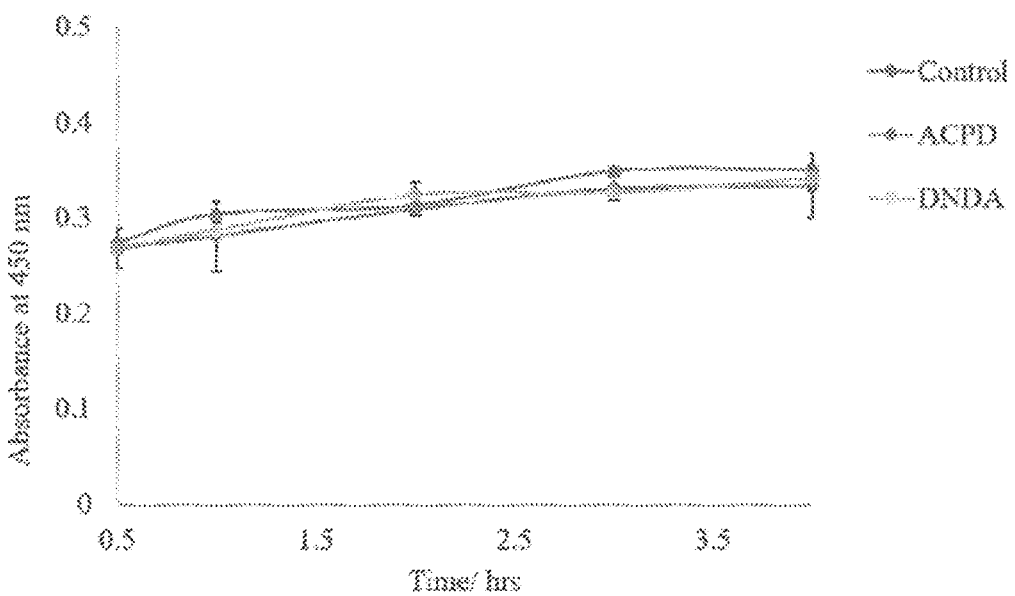
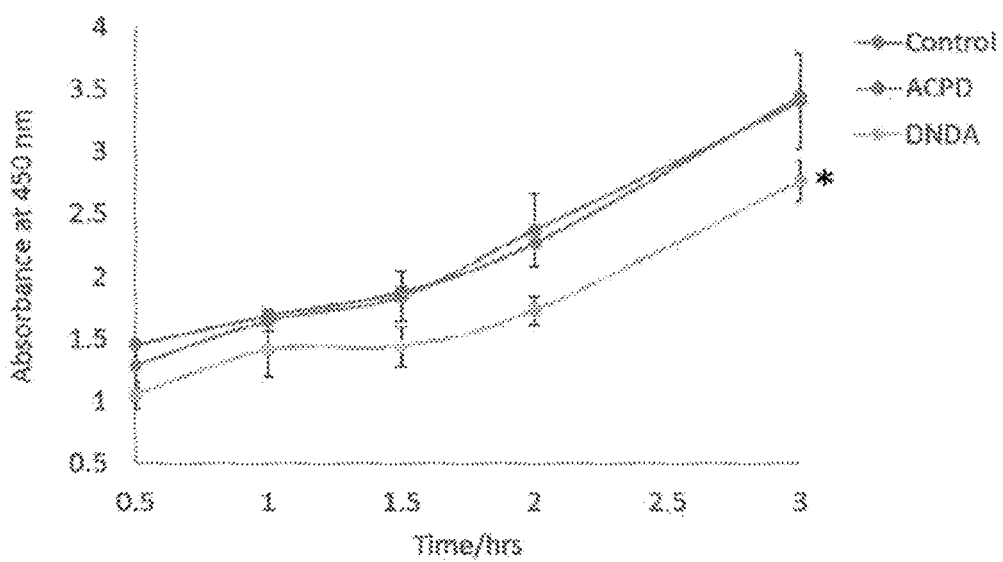
Figure 6A-B

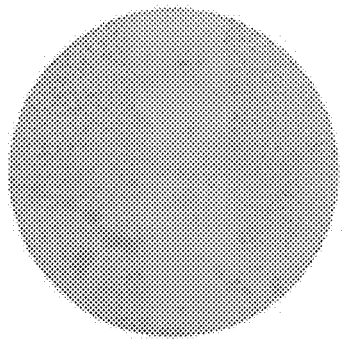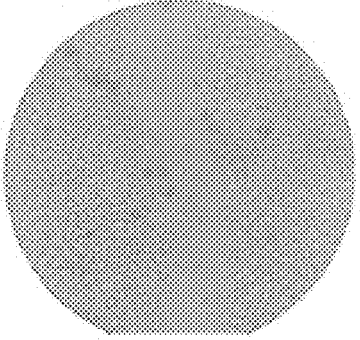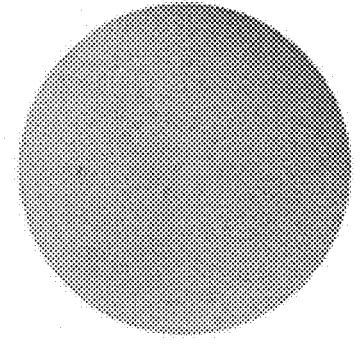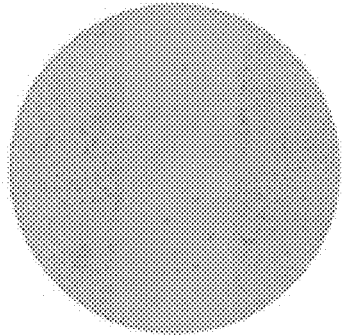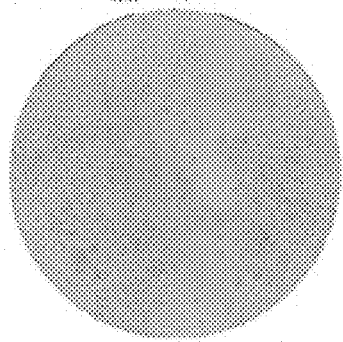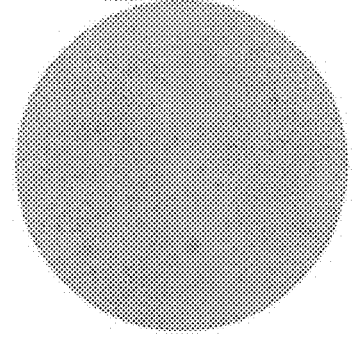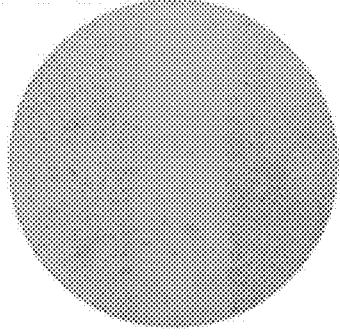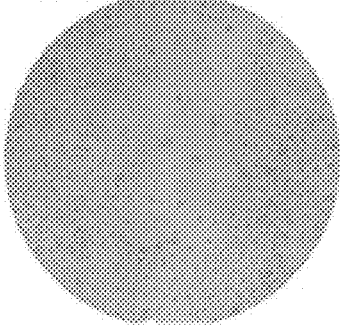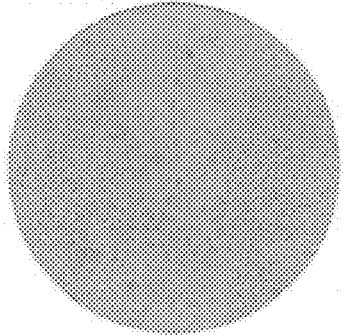
Fig. 7A

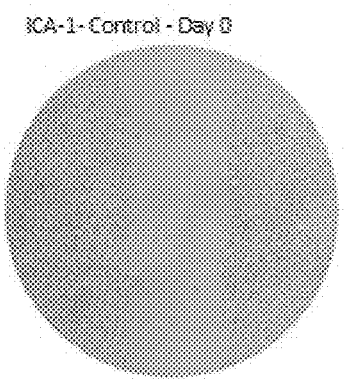
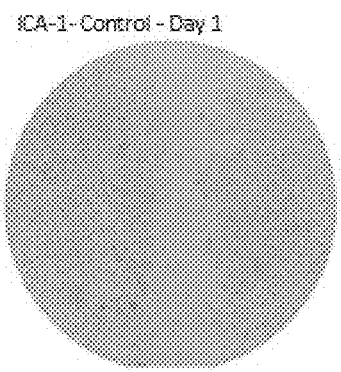
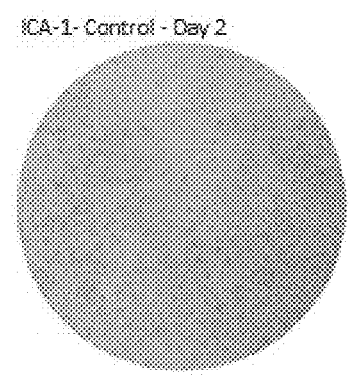
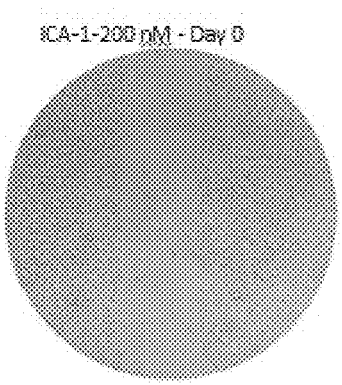
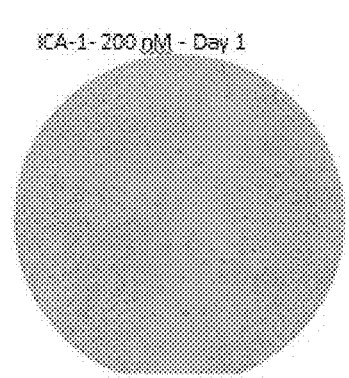
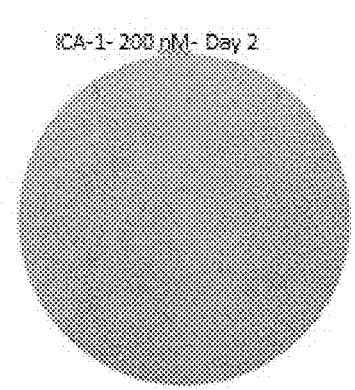
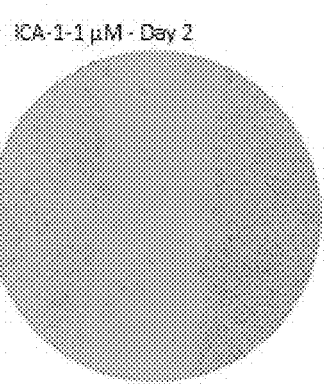
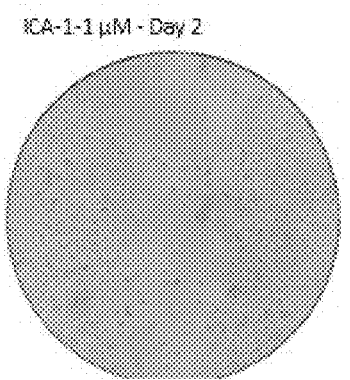
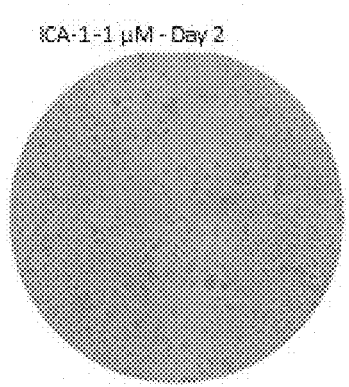
Fig. 7B

A.

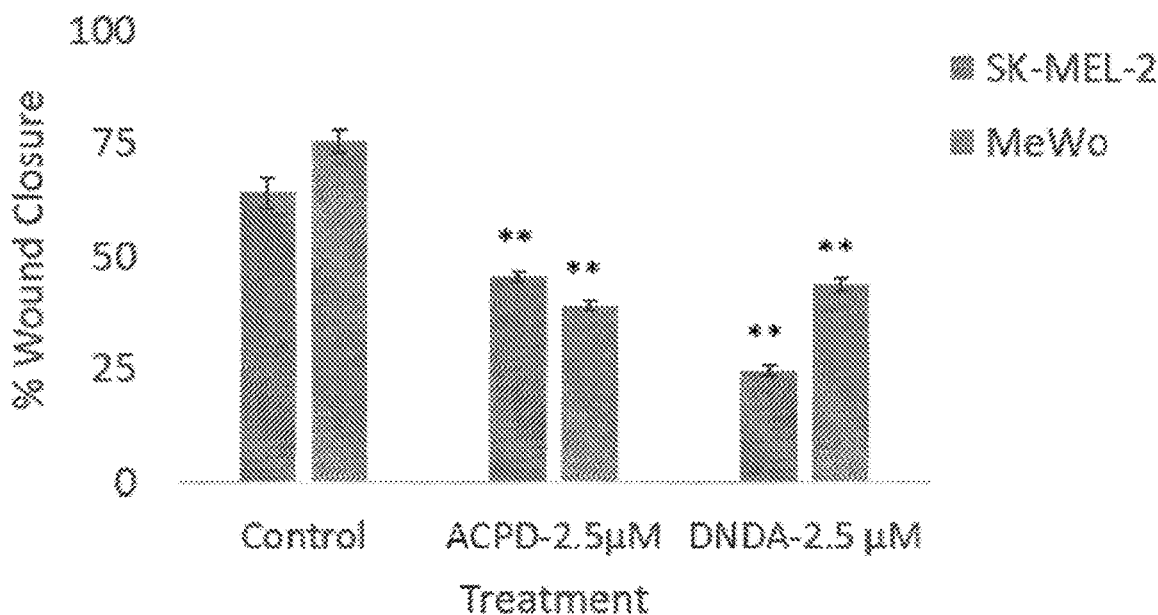
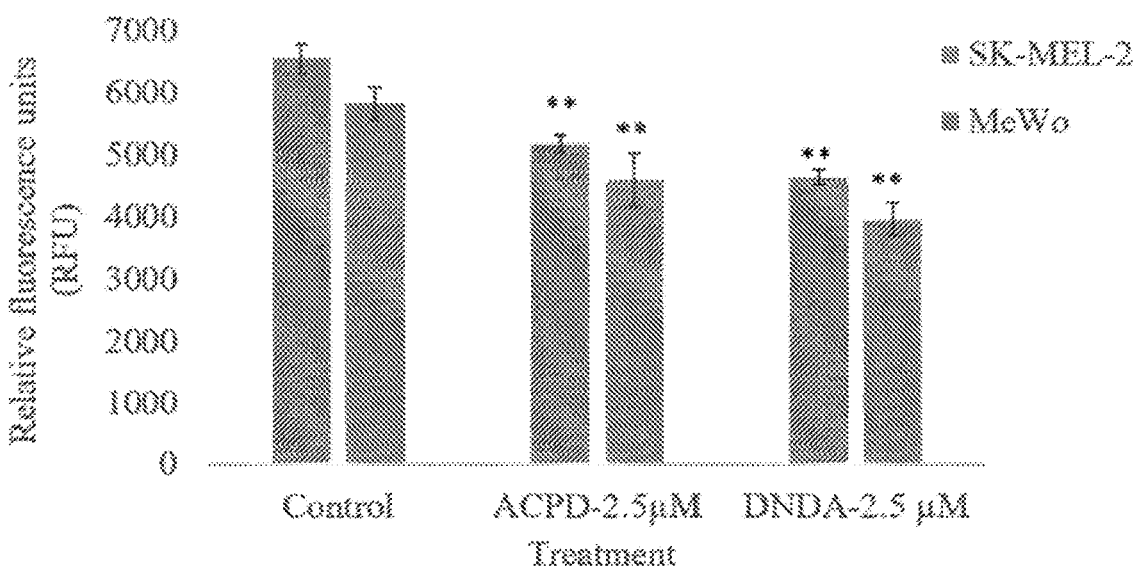
Figure 8C-D

A.
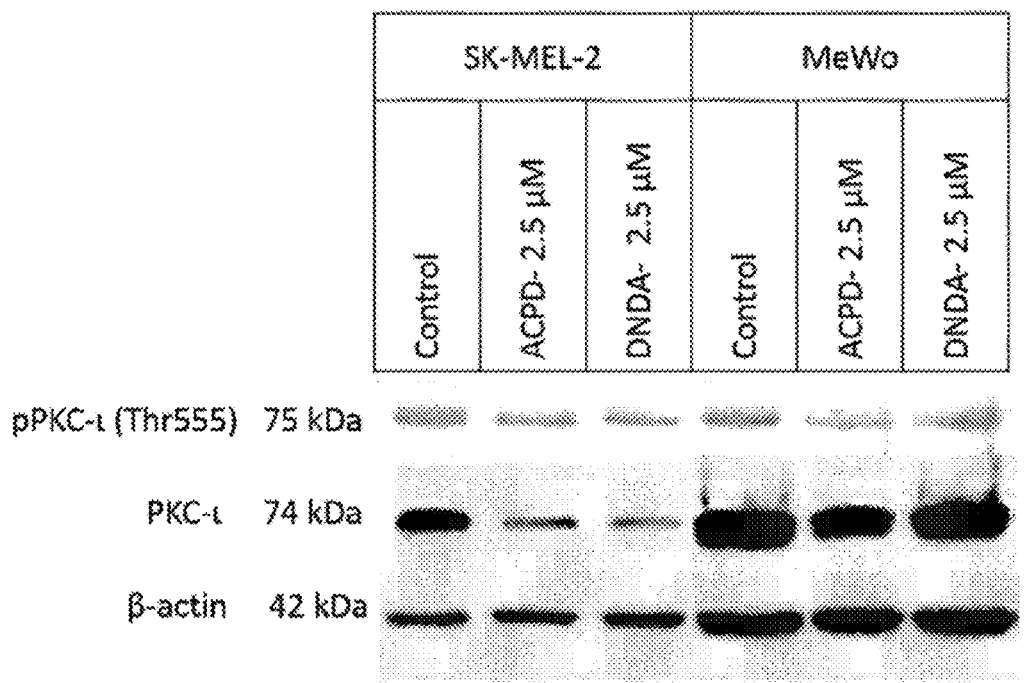
B.
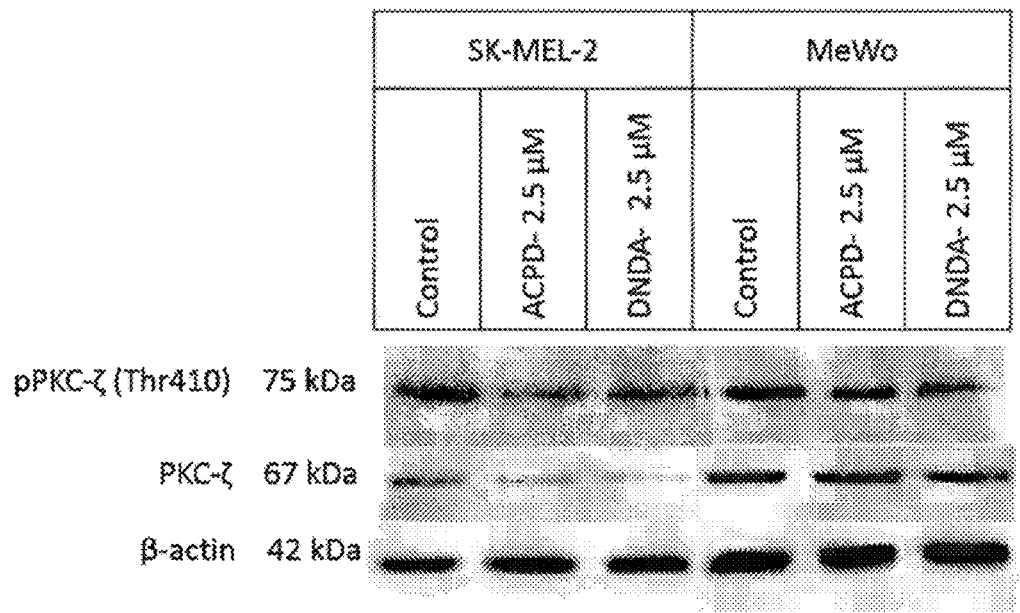
Figure 10A-B

A.
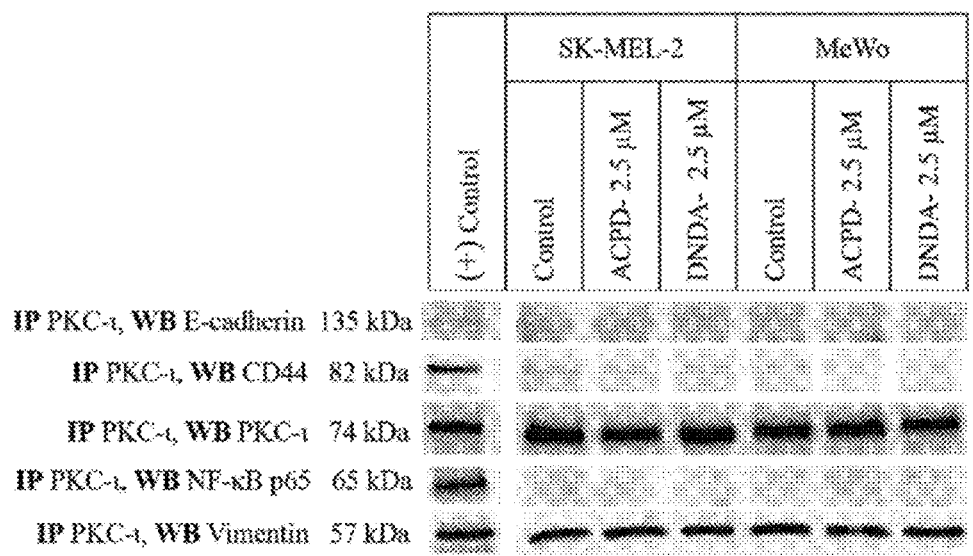
B.
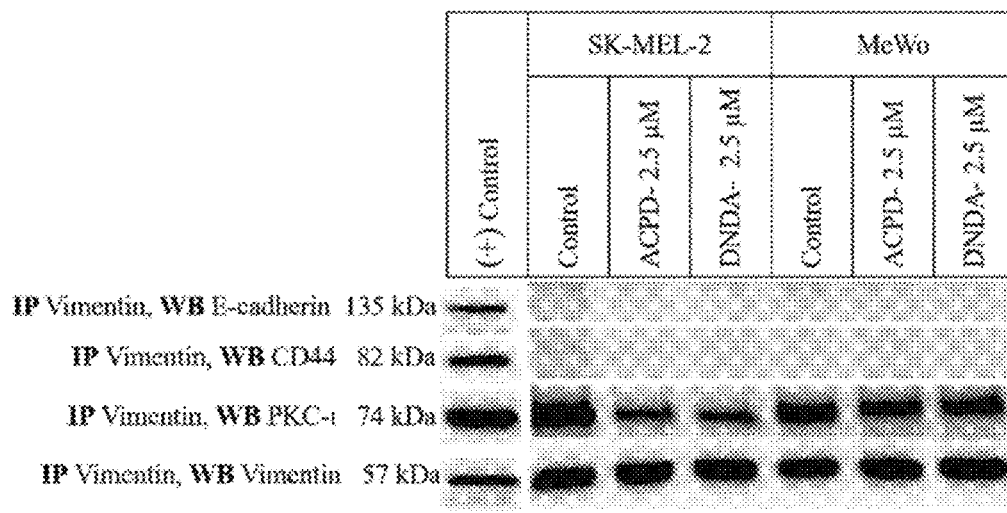
Figure 13A-B

A.
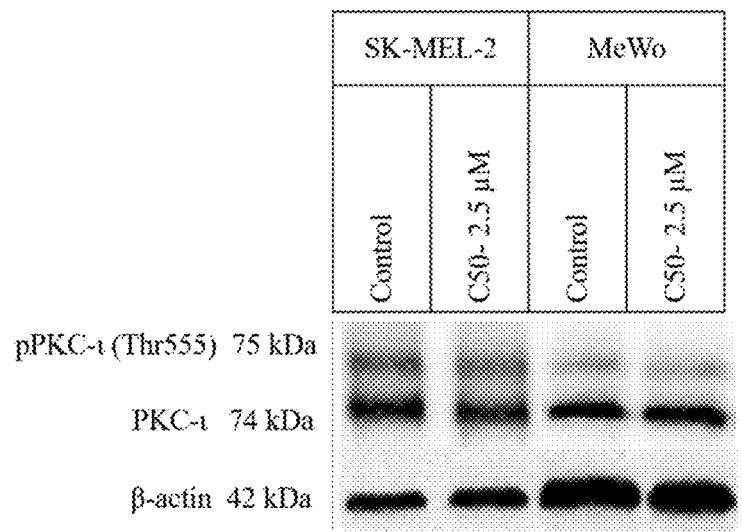
B.
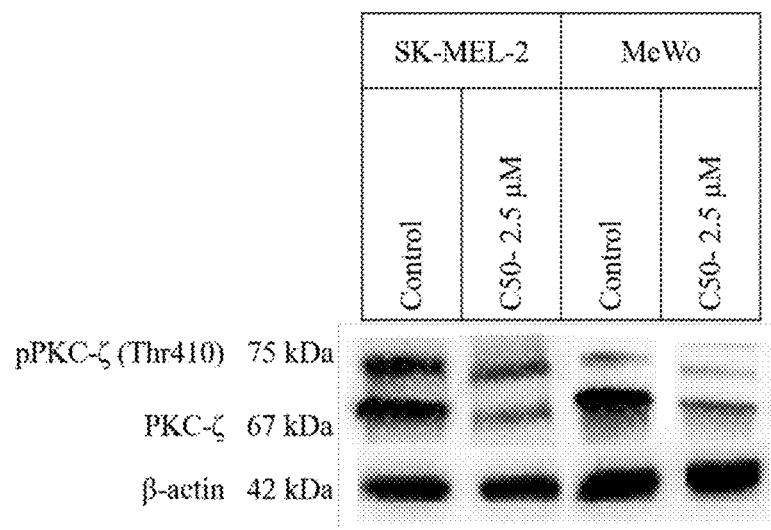
Figure 18A-B

METHOD OF TREATING MELANOMA USING AN INHIBITOR OF AN ATYPICAL PROTEIN KINASE C

CROSS-REFERENCE TO A RELATED APPLICATIONS

This application is a divisional of U.S. application Ser. No. 15/612,642, filed Jun. 2, 2017; which claims the benefit of U.S. Provisional Application Ser. No. 62/344,747, filed Jun. 2, 2016; and 62/453,751, filed Feb. 2, 2017, the disclosures of each of which are hereby incorporated by reference in their entirety, including all figures, tables and drawings.

BACKGROUND OF THE INVENTION

Melanoma is a type of cancer that occurs in melanocytes. The majority of melanoma occurs in skin; however, melanoma can rarely arise from the mucosal surfaces or areas to which neural cells migrate, for example, eye, intestine, and mouth [1].

The number of melanoma cases reported is on the rise. Malignant melanoma is very common among Caucasian populations worldwide. New cases in these populations are expected to double every 10-20 years. Australians are affected the most and New Zealand, Sweden, USA and Denmark follows thereafter [2]. According to the NIH Surveillance, Epidemiology and End Results (SEER) program, 76,380 new cases and 10,130 number of deaths due to melanoma were reported in 2016 in the USA. The number of new cases of melanoma of the skin was 21.6 per 100,000 men and women per year. The number of deaths was 2.7 per 100,000 men and women per year in USA. The current percent survival rate for 5 years is 91.5%. Out of that, only 4% survived once the melanoma has metastasized. Melanoma is more common in men than women and among individuals of fair complexion and those who have been exposed to sunlight over long periods of time [3].

Surgical resection is the primary means to control melanoma and it improves the survival rate if the melanoma has not metastasized. If it has metastasized, applications of immunotherapy, biologic therapy, radiation therapy, or chemotherapy may improve survival [3]. Change of the shape or color of existing moles or appearance of a new lump anywhere on the skin can be early symptoms of melanoma. At later stages, the mole may itch, ulcerate or bleed [4].

BRAF gene mutation is the most frequent mutation in melanoma which is approximately 40% to 60% of malignant melanomas. BRAF harbors a single nucleotide transversion in BRAF [5]. BRAF is the gene that makes the protein serine/threonine-protein kinase B-Raf. The gene BRAF is also called proto-oncogene B-Raf and v-Raf murine sarcoma viral oncogene homolog B. B-Raf is a member of the Raf kinase family of growth signal transduction protein kinases and it plays an important role in regulating the MAP kinase/ERKs (mitogen-activated protein kinases/extracellular signal-regulated kinases) signaling pathway, which affects cell division, differentiation, and secretion [6]. The most frequent mutation of BRAF in melanoma is the substitution of valine to glutamic acid at position 600 and a less frequent mutation includes valine 600 to lysine or arginine residues.

Apart from BRAF mutation, an alternative reading frame mutation of CDKN2A (cyclin-dependent kinase Inhibitor 2A) gene affects the destabilization of transcription factor p53 (tumor protein p53). This mutation could alter apoptosis in many cancers. Another mutation in the same gene leads to production of nonfunctional inhibitor for CDK4 (cyclin-dependent kinase 4) which promotes cell division [7, 8].

Protein Kinase C

PKCs are involved in controlling the function of other proteins in many signal transduction cascades through phosphorylation of hydroxyl groups of serine and threonine amino acid residues in those proteins [9]. These kinases are activated by several extracellular signals. PKC activating intracellular signals are elevated calcium and diacylglycerol (DAG). Additionally, secondary messengers like phorbol esters and co-factors such as phosphotidylserine also act as PKC activators [10-12].

Currently there are 15 PKC isozymes identified in humans. The term "protein kinase C (PKC)" refers to the entire family of isoforms. They are categorized into 3 sub families depending on the secondary messenger requirements. They are classical (conventional), novel and atypical. Conventional (c)PKCs contain the isoforms PKC-α (alpha), PKC-βI (beta 1), PKC-βII (beta 2) and PKC-γ (gamma). They require $Ca^{2+}$, DAG, and phosphatidylserine for the activation.

Novel (n)PKCs include the isoforms PKC-δ (delta), PKC-ε (epsilon), PKC-η (eta), and PKC-θ (theta). nPKCs require DAG for the activation but independent of $Ca^{2+}$. Both conventional and novel PKCs are activated through the same signal transduction pathway through phospholipase C. Atypical (a) PKCs include PKC-ζ (zeta) and PKC-ι (iota) or PKC-λ (lamda); mouse homologue of PKC-ι. aPKCs do not require either $Ca^{2+}$ or diacylglycerol for activation [12, 13].

In normal melanocytes, PKC-ζ was found in low levels and PKC-ι was not detected. But both proteins were detected in very high levels in malignant melanoma [14].

All PKC isozymes consist of a regulatory domain (N terminal) and a catalytic domain (C terminal) connected together by a hinge region. The catalytic region is highly conserved among the different isoforms. The second messenger requirement differences in the isoforms are due to the regulatory region difference among the classes (classical, novel and atypical). Apart from PKC-θ and PKC-ι, most of the crystal structures of the catalytic region of PKC have not been determined [15].

The regulatory domain of the PKCs contains several similar sub regions. The C1 domain is common to all of the conventional and novel PKC isoforms and it has a binding site for DAG as well as non-hydrolysable, non-physiological analogues called phorbol esters. C1 domain in both conventional and novel PKCs is capable of binding DAG but in atypical PKCs, it is incapable of binding to DAG or phorbol esters. The C2 domain is similar in both conventional and novel PKCs and it serves as a $Ca^{2+}$ sensor. It functions only in conventional PKCs. The pseudosubstrate region, which is present in all three classes of PKC, is a small sequence of amino acids that mimics a substrate and binds to the substrate-binding cavity in the catalytic domain. Lack of serine and threonine phosphor acceptor residues, keeps the enzyme inactive.

Phosphorylation at the catalytic region and release of pseudosubstrate from the regulatory region are required for the activation of PKC. When $Ca^{2+}$ and DAG are present in sufficient concentrations, they bind to the C2 and C1 domain and direct PKC to the membrane. This interaction within the membrane results in release of the pseudosubstrate from the catalytic site and activation of the enzyme. For these allosteric interactions to occur, however, PKC must first be properly folded to the correct conformation which allows for catalytic action. On extracellular stimulation such as increase in Ca$^{2+}$ concentration and DAG concentration, phospholipase C mediates the breakdown of phosphotidylinositol into phosphatidylinositol-3-kinase (PI3K) and DAG which causes the necessary conformational changes in the PKC structure and leads to release of the pseudosubstrate. Even though the activation of classical PKCs have been well explained, activation of other isozymes is not explained in detail. In classical PKCs, phosphatidylinositol-dependent-kinase (PDK-1) phosphorylates Thr-500 which initiates the auto-phosphorylation of PKC on Thr-641 and Ser-660. This process releases calcium ions from internal stores thereby activating PKC as discussed above [16]. Additionally, increased auto-phosphorylation of PKC-ζ leads to the activation of AMPK (5'-AMP-activated kinase) by peroxynitrite (ONOO$^-$) [17]. Thr-555/560 in PKC-ι and PKC-ζ is required for the activation of AMPK in insulin signaling in hepatocytes of type 2 diabetic humans [18].

Atypical PKC (aPKC)

aPKCs contains two structurally and functionally distinct isozymes in human. PKC-ι and PKC-ζ are the human homologs of the mouse PKC-λ (lamda). aPKCs do not have the C2 domain and therefore they are insensitive to calcium ions, DAG and phorbol esters which act as activators to other PKCs (classical and novel). aPKCs have only one cysteine rich or zinc finger like domain in the pseudosubstrate and this structural feature leads to the absence of C2 domain. The amino acid sequences in both PKC-ι and PKC-ζ are very similar to each other [19]. PKC-ι is encoded by the PRKCI gene and PKC-ζ is encoded by the PRKCZ gene. They are believed to be involved in cell cycle progression, tumorigenesis, cell survival and cell migration. Also, aPKCs play important roles in insulin-stimulated glucose transport [17, 18]. PKC-ι specifically has a strong influence on cell cycle progression. Additionally, it is involved in changing the cell polarity in cell division. Lung cancer cell proliferation is highly dependent on the PKC-ι level since it increases tumor cell proliferation by activating ERK1 pathway [19]. PKC-ι and PKC-ζ are expressed in both transformed and malignant melanoma [20]. Overexpression of PKC-ι plays an important role in the chemoresistance of leukemia [21]. PKC-ι is involved in glioma cell proliferation by regulating by phosphorylation of cyclin dependent kinase activating kinase/cyclin dependent kinase 7 pathway [22, 23].

PKC Isoform Status in Melanoma and Normal Melanocytes.

Since phorbol esters are essential to the in vitro growth of melanocytes, PKC isoforms in normal melanocytes and melanoma cells are of interest. Phorbol esters act as activators for conventional PKC isoforms. Selzer et. al. investigated the presence of 11 PKC isoforms in 8 different melanoma metastases, 3 normal melanocyte cell lines and 3 spontaneously transformed melanocytes. PKC-α, PKC-βI, PKC-βII, PKC-δ, PKC-ε, PKC-η, PKC-ζ and PKC-ι were found in all melanoma metastases samples. PKC-α, PKC-βI and PKC-ζ isoforms were found in both of normal melanocytes and transformed melanocytes. PKC-βII and PKC-ι were not detected in normal melanocytes. PKC-γ and PKC-θ isoforms were undetectable in all samples. PKC-ι was detected in increased amounts in both transformed melanocytes and melanoma metastases [20].

Comparison of Different Cell Signaling Pathways Involved in Cell Motility in Melanoma.

The Wnt5A/Protein Kinase C Pathway.

Published results show that Wnt5a associates with cytoskeletal changes through activation of PKC isoforms but is independent of β-catenin. In this pathway, KISS-1 (kisspeptin) act as a metastasis suppressor which inhibits the motility of cells via down regulation of Wnt5a. CD44 (antigen CD44) is involved in tumor cell homing during metastasis [24, 25]. CD44 is a cell-surface glycoprotein involved in cell-cell interactions, cell adhesion and migration in humans.

Vimentin is associated with EMT (Epithelial to Mesenchymal Transition). This decreases E-Cadherin due to upregulation of the transcriptional repressor Snail [24, 25]. KISS-1 inhibits Calcium regulated Calcineurin (calcineurin and GSK3B are in balance). KISS-1 is a metastasis suppressor of melanoma by micro-cell-mediated chromosomal transfer. KISS-1 signals via a G-protein receptor (Wnt5a also) GRP54 (activation of kisspeptin receptor). The effects of KISS-1/GRP54 signaling is directly opposed to Wnt5A, resulting in deactivation of PKC. KISS-1 can inhibit Calcium-regulated genes such as Calcineurin. Calcineurin plays a role in tumor cell signaling via the dephosphorylation of nuclear factor of activating T-cells (NFAT) and is involved in tumor progression. CD44 is dependent upon both Ca$^{2+}$/calmodulin signaling and PKC activity. Cells that have an increased CD44 can lose CD44 expression when either PKC or Wnt5A is inhibited. This implicates Wnt5A/PKC signaling in the up-regulation of CD44, an important mediator of cancer cell metastasis. Wnt5A regulates the gene for vimentin, which codes for an intermediate filament protein. Up-regulation of vimentin is associated with the EMT which is very important in tumor cell metastasis. The change in morphology results in the up-regulation of the transcriptional repressor Snail (Zinc finger protein SNAI1), which suppresses E-cadherin. Snail levels are increased due to the up-regulation of genes such as MMP-2 and NOTCH4. Additionally Snail expression is dependent upon PKC activation [24].

Cell Migration and Invasion Through the NF-κB1 Pathway.

Nuclear factor-κB (NF-κB)/Rel proteins include NF-κB2 p52/p100, NF-κB1 p50/p105, c-Rel, RelA/p65, and RelB. These proteins act as dimeric transcription factors that regulate the expression of genes in many biological pathways including cell motility. In the classical (or canonical) pathway, NF-κB/Rel proteins are bound and inhibited by IκB (inhibitors of kB) proteins. Proinflammatory cytokines, lipopolysaccharides (LPS), growth factors, and antigen receptors activate the IKK (IkB kinase) complex (IKKβ, IKKα, and NEMO), which phosphorylates IκB proteins. Phosphorylation of IκB leads to its ubiquitination and proteasomal degradation, freeing NF-κB/Rel complexes [26].

Active NF-κB/Rel complexes are further activated by post-translational modifications (phosphorylation, acetylation, glycosylation). PKC-ζ plays an important role in phosphorylation and translocation to the nucleus where, either alone or in combination with other transcription factors including AP-1, Ets, and Stat, they induce target gene expression [27]. In the alternative (noncanonical) NF-κB pathway, NF-κB2 p100/RelB complexes are inactive in the cytoplasm. Signaling through a subset of receptors, including LTβR, CD40, and BR3, activates the kinase NIK, which in turn activates IKKα complexes that phosphorylate C-terminal residues in NF-κB2 p100. Phosphorylation of NF-κB2 p100 leads to its ubiquitination and proteasomal processing to NF-κB2 p52. This creates transcriptionally competent NF-κB p52/RelB complexes that translocate to the nucleus and induce target gene expression [28, 29].

MMP-2 (matrix metalloproteinase) and VEGFA (vascular endothelial growth factor A) are believed to be upregulated NF-κB1 p50/p105 in tumor invasion and metastasis of uveal melanoma [29].

The Wnt-aPKC Signaling Pathway.

WntWnt/Fz signaling via Dvl (polarity proteins dishevelled) induces aPKC activation, possibly via Dvl association with the aPKC/Par3/Par6 complex. aPKC phosphorylates and inhibits Par1/MARK2 kinase, which regulates microtubules. Dvl also associates with Lgl, which is antagonistic to aPKC. This Wnt signaling regulates epithelial and neuronal polarity and cell migration. Axin and APC may be involved [30, 31, 32].

The Rho Pathway.

Atypical PKCs are involved in the regulation of cancer cell migration and invasion. PKC-ζ dependent phosphorylation of RhoGDI-1 (Rho GDP-dissociation inhibitor) and subsequent activation of RhoGTPases, is the mechanism that mediates superoxide-induced cell migration. Although there are other forms of PKCs, only PKC-ζ formed a complex with RhoGD1, which is further enhanced by superoxide stimulation. EGF can induce PKC-ζ translocation from the cytosol to the plasma membrane and activation of PKC-ζ probably via PI3K (Phosphatidylinositol-4, 5-bisphosphate 3-kinase). PKC-ζ is an essential component of the EGF-stimulated chemotactic signaling. The myristoylated PKC-ζ peusosubstrate peptide blocked the chemotaxis. PTEN (Phosphatase and tensin homolog) deficiency results in a marked increase in cell invasiveness that can be suppressed by a PKC-ζ specific pseudosubstrate peptide inhibitor [33, 34]. PTEN is a protein that, in humans, is encoded by the PTEN gene it acts as a phosphatase to dephosphorylate PI3K.

PKC Inhibitors

PKC inhibitors range in their selectivity for a particular class of PKCs. Only aPKC family may contain the PB 1 domain and thus agents that disrupt signaling through this mechanism should be specific for atypical PKCs. Sodium aurothiomalate (ATM) and aurothioglucose (ATG) both seem to bind in the low micromolar range to PKC-ι, and as such, may be alternatives for PKC-ι specific inhibitors. Another gold-containing drug, auranofin, has a similar structure and thus may also have potential as a PKC inhibitor. Structures for certain examples of the gold-containing PKC-ι inhibitors are described in, for example, U.S. Pat. No. 9,301,965.

PKC-ι inhibitor [4-(5-amino-4-carbamoylimidazol-1-yl)-2,3-dihydroxycyclopentyl]methyl dihydrogen phosphate, known as (ICA-1), is a small molecule inhibitor which binds to the catalytic domain of human PKC-ι, at amino acid residues 469-475 (glutamine-469, isoleucine-470, arginine-471, isoleucine-472, proline-473, arginine-474, serine-475). ICA-1 is an inhibitory agent specific to PKC-ι. Structure of ICA-1 is shown below.

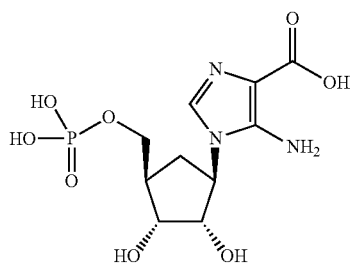 [SMILES: Nc1c(C(=O)O)ncn1[C@@H]1C[C@H](COP(=O)(O)O)[C@@H](O)[C@H]1O]

2-acetyl-1,3-cyclopentanedione (ACPD) is a pan-aPKC inhibitor which inhibits both PKC-ζ and PKC-ι, but not PKC-α, PKC-β, PKC-δ, or PKC-ε. The structure of ACPD is shown below:

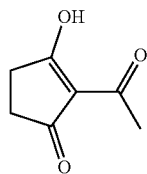

Pachastrissamine and its stereoisomers have demonstrated cytotoxic effects on several cancer cell lines with potencies in the submicromolar range. Complete inhibition of both PKC-ζ and PKC-ι at 10 μM has been observed with only modest effects for novel and classical PKC isoforms. Screening at lower concentrations showed about 50% inhibition at 3 μM and no inhibition at 1 μM. Structures for pachastrissamine and its stereoisomers are described in, for example, U.S. Pat. No. 9,301,965.

A 13-mer PKC-ζ inhibitory peptide (ZIP) is myristoylated at the N-terminus to improve cell penetration and may serve as a novel PKC-ζ specific therapeutic. Structure of ZIP is also described in, for example, U.S. Pat. No. 9,301,965.

A series of speciosterosulfates (sterolsulfates), isolated from the marine sponge Spheciospongia, have been found to inhibit PKC-ζ. Structures for speciosterosulfates are described in, for example, U.S. Pat. No. 9,301,965.

Several allosteric inhibitors which bind the PIF-1 site and regulate activity through the C1 domain as well as a series of phenylthiopenes may also have implications as potential aPKC inhibitors. Structures for certain examples of the allosteric inhibitors and the phenylthiopenes are shown in, for example, U.S. Pat. No. 9,301,965.

Other potential PKC inhibitors include, but are not limited to: a compound containing a maleimide substructure; a series of compounds having an indazole-benzimidazole motif; a series of ATP-competitive thieno[2,3-d]pyrimidine analogues (26-27); a pyrrole amide PKCzI257.3; and a series of 3-hydroxy-2-(3-hydroxyphenyl)-4H-1-benzopyran-4-ones which may bind to the ATP-cleft of the kinase through a keto-hydroxyl motif in multiple conformations. Structures for the above listed potential PKC inhibitors are shown in, for example, U.S. Pat. No. 9,301,965.

A preferred atypical PKC inhibitor of subject invention is 8-hydroxy-1, 3,6-naphthalenetrisulfonic acid (ζ-Stat) which is specific to PKC-ζ. The structure of ζ-Stat is shown below:

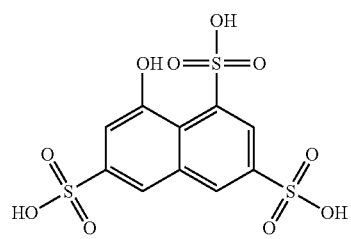 [SMILES: O=S(=O)(O)c1cc(O)c2c(S(=O)(=O)O)cc(S(=O)(=O)O)cc2c1]

BRIEF SUMMARY OF THE INVENTION

The invention relates to a method of treating melanoma by administering to a subject in need thereof, a composition comprising a therapeutically effective amount of an inhibitor of an aPKC, for example, PKC-ζ and PKC-ι. An inhibitor of an aPKC useful in the methods of the invention can inhibit PKC-ζ and/or PKC-ι. Non-limiting examples of an inhibitor of PKC-ζ and/or PKC-ι include ICA-1, ACPD, and ζ-Stat.

A further embodiment of the invention provides PKC-ζ and/or PKC-ι as a biomarker for identifying a melanoma in a subject as likely to be responsive to a therapy using an inhibitor of aPKC. Accordingly, a method of identifying a subject having a melanoma as being responsive or non-responsive to a melanoma therapy with an inhibitor of PKC-ζ and/or PKC-ι based on the levels and/or activity of PKC-ζ and/or PKC-ι mRNA or protein in the melanoma cells from the subject are also provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows an image depicting the chemical structure of ACPD. FIG. 1 B shows an image depicting the chemical structure of DNDA.

FIG. 5A shows the effect of aPKC inhibitors ACPD and DNDA on PCS-200-013 cell number. FIG. 5B shows the effect of ACPD on SK-MEL-2 cell number. FIG. 5C shows the effect of DNDA on SK-MEL-2 cell number. FIG. 5D shows the effect of ACPD on MeWo cell number.

FIG. 6A shows cell proliferation as measured by the WST-1 assay for MEL-F-Neo cells. FIG. 6B shows cell proliferation as measured using the WST-1 assay for SK-MEL-2 cells.

FIG. 7A shows a wound healing assay for SK-MEL cells in the absence and presence of ACPD. FIG. 7B shows a wound healing assay for SK-MEL cells in the absence and presence of ICA-1.

FIG. 8C shows a comparison of the calculated percent wound closure as measured in the wound healing assay. FIG. 8D shows a comparison of the calculated percent cell invasion as measured in a Boyden chamber assay.

FIG. 10A shows the change in the levels of phosphorylated and total PKC-ι in the absence and presence of aPKC inhibitors ACPD and DNDA in SK-MEL-2 and MeWo cells. FIG. 10B shows the change in the levels of phosphorylated and total PKC-ι in the absence and presence of aPKC inhibitors ACPD and DNDA in SK-MEL-2 and MeWo cells.

FIG. 13A shows the immunoprecipitation of PKC-ι and western blots of associated vimentin, E-cadherin, CD44, and NF-κB p65. FIG. 13B shows the immunoprecipitation of vimentin and western blots of associated E-cadherin, CD44, and PKC-ι.

FIG. 18A shows the effects of ζ-Stat on expression of PKC-ι in SK-MEL-2 cells. FIG. 18B shows the effects of ζ-Stat on expression of PKC-ζ in MeWo cells.

DETAILED DISCLOSURE OF THE INVENTION

Figure 1C:
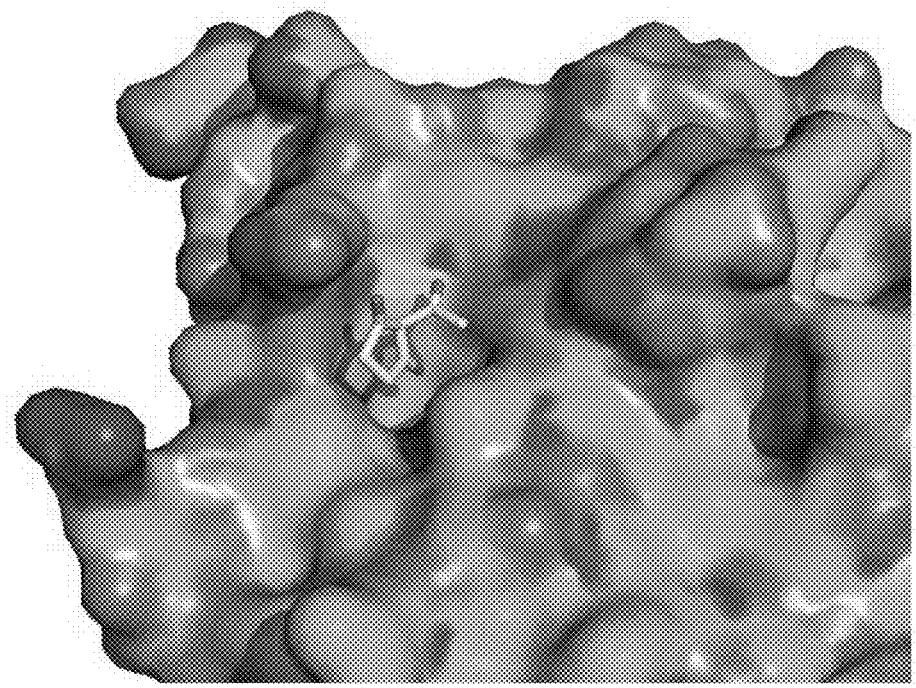
FIG. 1C shows an image depicting the molecular docking of ACPD on PKC-ι.

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the terms "about" or "approximately" are used, these compositions contain the stated amount of the ingredient with a variation (error range) of 0-10% around the value (X±10%).

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the PKC inhibitors described herein, its use in the compositions of the invention is contemplated.

"Treatment", "treating", "palliating" and "ameliorating" (and grammatical variants of these terms), as used herein, are used interchangeably. These terms refer to an approach for obtaining beneficial or desired results including but not limited to therapeutic benefit. A therapeutic benefit is achieved with the eradication or amelioration of one or more of the physiological symptoms associated with the underlying cancer such that an improvement is observed in the subject, notwithstanding that the subject may still be afflicted with the underlying cancer. A treatment includes delaying the appearance of a disease or condition, delaying the onset of symptoms of a disease or condition, slowing, halting, or reversing the progression of a disease or condition, or any combination thereof. As used herein, the term "cancer" refers to the presence of cells possessing abnormal growth characteristics, such as uncontrolled proliferation, immortality, metastatic potential, rapid growth and proliferation rate, perturbed oncogenic signaling, and certain characteristic morphological features. This includes but is not limited to the growth of: (1) benign or malignant cells (e.g., tumor cells) that correlates with overexpression of a serine/threonine kinase; or (2) benign or malignant cells (e.g., tumor cells) that correlates with abnormally high levels of serine/threonine kinase activity or lipid kinase activity. Non-limiting serine/threonine kinases implicated in cancer include but are not limited to PI-3K mTOR, and AKT. Exemplary lipid kinases include but are not limited to PI3 kinases such as PBKα, PBKβ, PBKδ, and PBKγ.

The term "effective amount" or "therapeutically effective amount" refers to that amount of an inhibitor described herein that is sufficient to effect the intended application including but not limited to disease treatment. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

For the specific PKC-ι inhibitor ICA-1, the therapeutically effective concentration can be between about 800 nM to about 10 μM. In some embodiments the range of ICA-1 concentration is between about 1 μM to about 2 μM. In some embodiments, the therapeutically effective concentration of ICA-1 is about 2 μM.

For ACPD, the therapeutically effective concentration can be between about 800 nM to about 10 μM. In some embodiments, the therapeutically effective concentration was found to be about 2 μM. Therapeutically effective concentrations for other PKC-ι inhibitors can be readily determined by those of ordinary skill in the art.

The amount of ICA-1 or ACPD administered can be an amount from a low of about 0.8 μM, about 0.9 μM, or about 1 μM to a high of about 2 μM, about 5 μM, or about 10 μM. For example, the amount of ICA-1 or ACPD of the subject invention that inhibits growth of melanoma cells can be from about 0.8 μM to about 10 μM, from about 0.9 μM to about 5 μM, from about 1 μM to about 2 μM, from about 0.8 μM to about 5 μM, from about 0.8 μM to about 2 μM, from about 0.9 μM to about 10 μM, from about 0.9 μM to about 5 μM, from about 0.9 μM to about μM, from about 1 μM to about 10 μM, from about 1 μM to about 5 μM, from about 1 μM to about 2 μM, from about 1.5 μM to about 10 μM, from about 1.5 μM to about 5 μM, from about 1.5 μM to about 2 μM, from about 1.8 μM to about 10 μM, from about 1.8 μM to about 5 μM, from about 1.8 μM to about 2 μM.

For ζ-Stat, the therapeutically effective concentration can be between about 800 nM to about 20 μM. In some embodiments the range of ζ-Stat concentration is between about 1 μM to about 10 μM. In some embodiments, the therapeutically effective concentration of ζ-Stat is about 5 μM.

The amount of ζ-Stat administered can be an amount from a low of about 0.8 μM, about 0.9 μM, or about 1 μM to a high of about 2 μM, about 5 μM, about 10 μM, or about 20 μM. For example, the amount of ζ-Stat of the subject invention that inhibits growth of melanoma cells can be from about 0.8 μM to about 20 μM, from about 0.9 μM to about 10 μM, from about 1 μM to about 5 μM, from about 0.8 μM to about 10 μM, from about 0.8 μM to about 5 μM, from about 0.8 μM to about 2 μM, from about 0.9 μM to about 20 μM, from about 0.9 μM to about 5 μM, from about 0.9 μM to about 2 μM, from about 1 μM to about 20 μM, from about 1 μM to about 10 μM, from about 1 μM to about 2 μM, from about 1.5 μM to about 20 μM, from about 1.5 μM to about 10 μM, from about 1.5 μM to about 5 μM, from about 1.5 μM to about 2 μM, from about 1.8 μM to about 20 μM, from about 1.8 μM to about 10 μM, from about 1.8 μM to about 5 μM, from about 1.8 μM to about 2 μM.

A "sub-therapeutic amount" of a PKC inhibitor is an amount less than the effective amount for that inhibitor, but which when combined with an effective or sub-therapeutic amount of another therapeutic compound or therapy can produce a desired result, due to, for example, synergy in the resulting efficacious effects (e.g., therapeutic benefit) for the subject, or reduced side effects associated with the compounds administered to the subject. Typical therapeutic amounts for an agent, as disclosed herein, can be ascertained from various publicly available sources (e.g., drugs.com, The Physician's Desk Reference, or scientific literature). Subtherapeutic amounts of an inhibitor, as provided herein, are amounts less than those reported in the publicly available sources.

"Subject" refers to an animal, such as a mammal, for example a human. The methods described herein can be useful in both humans and non-human animals. In some embodiments, the subject is a mammal (such as an animal model of disease), and in some embodiments, the subject is human. The terms "subject" and "subject" can be used interchangeably.

The terms "simultaneous" or "simultaneously" as applied to administering therapies to a subject refer to administering one or more therapies at the same time, or at two different time points that are separated by no more than 30 minutes. The term "after or before" as applied to administering therapies to a subject refers to administering more than one doses at two different time points that are separated by more than 30 minutes, e.g., about 1 hour, about 2 hours, about 5 hours, 8 hours, 1 day, 2 days, 3 days, 4 days, 5 days, 6 days, 7 days or even longer.

The term "inhibitor" refers to a compound having the ability to inhibit a biological function of a target protein, whether by inhibiting the activity or expression of the target protein. Accordingly, the term "inhibitor" is defined in the context of the biological role of the target protein.

The term "PKC inhibitor" as used herein refers to an agent that inhibits the activity or reduces/inhibits the expression of one or more isoforms of PKC. Examples of such inhibitors include, but are not limited to, ICA-1, ACPD, fludarabine and derivatives thereof; aurothioglucose; aurothiomaleate; auranofin; thimerosal; phenylmercuric acetate; ebselen; cisplatin; taxol; apomorphine; pyrantel pamoate; gossypolacetic acid complex; ellagic acid; hexestrol; Pachastrissamine and its stereoisomers; ZIP; allosteric inhibitors which bind the PIF-1 site and regulate activity through the C1 domain; a series of phenylthiopenes; a compound containing a maleimide substructure; speciosterosulfates (sterolsulfates); a series of compounds having an indazole-benzimidazole motif; a series of ATP-competitive thieno[2,3-d] pyrimidine analogues; a pyrrole amide PKCzI257.3; and a series of 3-hydroxy-2-(3-hydroxyphenyl)-4H-1-benzopyran-4-ones which may bind to the ATP-cleft of the kinase through a keto-hydroxyl motif in multiple conformations; and derivatives thereof. Numbers in parentheses refer to the corresponding numbered structure of the agent listed in the Background section of the application. Certain examples of PKC inhibitors that can be used in the methods described herein are provided in the U.S. Pat. No. 9,301,965.

The term "pan-aPKC inhibitor" as used herein refers to an agent that inhibits the activity or reduces/inhibits the expression of at least one atypical PKC such as PKC-ι or PKC-ζ. Examples of such agents include, but are not limited to ACPD, pachastrissamine and its stereoisomers, and derivatives thereof.

The terms "PKC-ι inhibitor" as used herein refers to an agent that inhibits PKC-ι activity or reduces or inhibits expression of PKC-ι. The agent may be specific to PKC-ι or alternatively may be a pan-aPKC inhibitor that is effective against different aPKC isoforms, such as ACPD. The inhibitor can be a polypeptide that binds to a unique sequence in the catalytic domain of PKC-ι and inhibits its activity; a polypeptide that is involved with the interaction of PKC-ι with other signaling molecules; a polypeptide having sequence homology to a specific region of a signaling molecule that mediates the binding of these molecules to PKC-ι; or a small molecule inhibitor, such as ICA-1 and derivatives thereof.

The term "PKC-ζ inhibitor" as used herein refers to an agent that inhibits PKC-ζ activity or reduces or inhibits expression of PKC-ζ. The agent may be specific to PKC-ζ, such as ζ-Stat, or alternatively may be a pan-aPKC inhibitor that is effective against different aPKC isoforms, such as ACPD. The inhibitor can be a polypeptide that binds to a unique sequence in the catalytic domain of PKC-ζ and inhibits its activity; a polypeptide that is involved with the interaction of PKC-ζ with other signaling molecules; a polypeptide having sequence homology to a specific region of a signaling molecule that mediates the binding of these molecules to PKC-ζ; or a small molecule inhibitor. Examples of a PKC-ζ inhibitor include, but are not limited to, ZIP, ACPD, speciosterosulfates (sterolsulfates), and derivatives thereof.

In specific preferred embodiments of the subject invention, the novel atypical PKC inhibitor is specific to PKC-ζ. In more preferred embodiments, the novel atypical PKC inhibitor is 8-hydroxy-1, 3,6-naphthalenetrisulfonic acid (ζ-Stat).

"Administration" or "administering" is used to describe the process in which the PKC inhibitors of the present invention are delivered to a subject for treatment. This includes parental, referring to parenterally (intramuscularly, intraperitoneally, intraarterially, intravenously, subcutaneously), orally, topically, transdermally, or vaginally and other routes that allow the PKC inhibitor to contact the cancer cells. The PKC inhibitor may be administered independently or in combination with other compounds, such as other chemotherapeutic compounds.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

As noted above, the number of melanoma cases has increased every year. It is not totally understood which intracellular chemicals are involved in signaling pathways and that govern the metastasis of melanoma cancer cells. Even though PKC-ι was not reported in normal melanocytes, it was detected in exclusively high amounts in both transformed melanocytes and melanoma metastases. PKC-ζ was also reported in both normal melanocytes and melanoma metastases.

The methods disclosed in the subject invention disclose method to assess the effectiveness of ACPD on both PKC-ι and PKC-ζ ICA-1 as an inhibitor of PKC-ι, and ζ-Stat as inhibitor of PKC-ζ.

In some embodiments, SK-MEL-2 metastasis melanoma cells, MeWo metastasis melanoma cells and PCS-200-013 normal melanocyte cells are cultivated and treated with ACPD, ICA-1, and/or ζ-Stat in separate sets of flasks for three consecutive days while taking the cell count for every 24 hrs. In certain embodiment, statistically significant decreases in cell number in SK-MEL-2 cells and MeWo cells are observed while no change is observed in PCS-200-013.

In other embodiments of the subject invention, a scratch assay to test the degree of metastasis and western blotting analysis using cell lysates are provided to test the levels of PKC-ι and PKC-ζ. In said assays, the cell population of melanoma cells has an inversely proportional relationship with the drug concentrations. Therefore, an inhibitor of PKC-ι and/or PKC-ζ for example, ACPD, ICA-1, or ζ-Stat, decreases the cell population and motility of melanoma cancer cells and thus, can be used in the treatment of melanoma.

Accordingly, an embodiment of the invention provides a method of treating melanoma, the method comprising administering to a subject in need thereof, a therapeutically effective amount of an inhibitor of an aPKC, for example, PKC-ι and PKC-ζ. In one embodiment, the PKC inhibitor is specific to a single aPKC, for example, PKC-ι.

In certain embodiments, the specific inhibitor of PKC-ι is ICA-1. In other embodiments, the PKC inhibitor is a pan-aPKC inhibitor. In preferred embodiments, the pan-PKC inhibitor is ACPD.

In certain embodiments, the specific inhibitor of PKC-ζ is ζ-Stat.

In further embodiments, methods of inhibiting melanocyte proliferation are provided. In preferred embodiments, the methods comprise contacting the melanocyte with a therapeutically effective amount of an inhibitor of an aPKC, for example, PKC-ι and PKC-ζ.

In some embodiments, the PKC inhibitor is specific to a single aPKC, for example, PKC-ι. In a preferred embodiment, the specific inhibitor of PKC-ι is ICA-1.

In other embodiments, the PKC inhibitor is a pan-aPKC inhibitor. In preferred embodiments, the pan-aPKC inhibitor is ACPD.

In yet other embodiments, the PKC inhibitor is specific to a single aPKC, for example, PKC-ζ. In a preferred embodiment, the specific inhibitor of PKC-ζ is ζ-Stat.

Advantageously, it was determined that ζ-Stat interacts with amino acid residues of 251-547 (I251, R253, V259, K274, D544, and F547) of the catalytic domain of PKC-ζ and that ζ-Stat is specific only to PKC-ζ.

In further embodiments, aPKC, including, but not limited to, PKC-ι and/or PKC-ζ, can be used as a biomarker for identifying a melanoma subject as being responsive to a treatment with an aPKC inhibitor.

In some embodiment, melanoma cells from a subject having melanoma exhibit a higher expression and/or amount of mRNA or protein for PKC-ζ and/or PKC-ι. In preferred embodiments, the melanoma cells of said subject are responsive to a melanoma therapy with an inhibitor of aPKC.

In a specific embodiment, the subject invention provides a method for identifying a subject as responsive or non-responsive to a melanoma therapy with an inhibitor of an aPKC based on higher expression and/or amount of mRNA or protein for PKC-ζ and/or PKC-ι in melanoma cells from the subject compared to a control.

The phrase "a subject is responsive to a melanoma therapy" indicates that upon administration of the melanoma therapy, the subject exhibits beneficial or desired results including but not limited to therapeutic benefit; eradication, amelioration, delay or prevention of one or more of the symptoms of melanoma; prolonging the life-span of the subject; or improvement in the quality of life of the subject. An improvement may be observed in the patient, notwithstanding that the patient may still be afflicted with melanoma.

The phrase "a subject is non-responsive to a melanoma therapy" indicates that upon administration of the melanoma therapy, the subject does not exhibit beneficial or desired results such as, therapeutic benefit; eradication, amelioration, delay or prevention of one or more of the symptoms of melanoma; prolonging the life-span of the subject; or improvement in the quality of life of the subject.

It was advantageously determined that a subject having a melanoma wherein the melanoma cells from the subject exhibit a higher level and/or activity of mRNA or protein for PKC-ζ and/or PKC-ι is responsive to a melanoma therapy with an inhibitor of PKC-ζ and/or PKC-ι.

Accordingly, in preferred embodiments of the subject invention, methods are provided for identifying a subject as responsive or non-responsive to a melanoma therapy with an inhibitor of PKC-ζ and/or PKC-ι based on higher level and/or activity of mRNA or protein for PKC-ζ and/or PKC-ι in the melanoma cells from the subject compared to a control.

In a certain embodiment, the subject invention provides a method of identifying a subject suffering from a melanoma as responsive or non-responsive to a therapy with an inhibitor of PKC-ζ and/or PKC-ι. The method comprises the steps of:

(a) determining the level and/or activity of PKC-ζ and/or PKC-ι mRNA or protein in a test sample obtained from the subject, (b) optionally, determining the level and/or activity of PKC-ζ and/or PKC-ι mRNA or protein in a control sample, or obtaining a reference value corresponding to the level of PKC-ζ and/or PKC-ι mRNA or protein; and (i) identifying the subject as being responsive to the melanoma therapy with the inhibitor of PKC-ζ and/or PKC-ι based the level and/or activity of PKC-ζ and/or PKC-ι mRNA or protein in the test sample as compared to the level and/or activity of PKC-ζ and/or PKC-ι mRNA or protein in the control sample, and optionally, administering the melanoma therapy with the inhibitor of PKC-ζ and/or PKC-ι to the subject identified as being responsive; or (ii) identifying the subject as being non-responsive to the melanoma therapy with the inhibitor of PKC-ζ and/or PKC-ι based the level and/or activity of PKC-ζ and/or PKC-ι mRNA or protein in the test sample as compared to the level and/or activity of PKC-ζ and/or PKC-ι mRNA or protein in the control sample, and optionally, administering a melanoma therapy other than the melanoma therapy with the inhibitor of PKC-ζ and/or PKC-ι to the subject identified as being non-responsive.

In specific embodiments, the test samples comprise the melanoma cells from the subject.

It was advantageously determined that a subject's melanoma is responsive to a melanoma therapy with an inhibitor of PKC-ζ and/or PKC-ι if the melanoma cells in the subject contain a higher level and/or activity of mRNA or protein for PKC-ζ and/or PKC-ι in the melanoma cells from the subject compared to a control sample of non-melanoma cells.

It was also determined that a subject's melanoma is non-responsive to a melanoma therapy with an inhibitor of PKC-ζ and/or PKC-ι if the melanoma cells in the subject contain a similar or lower level and/or activity of mRNA or protein for PKC-ζ and/or PKC-ι in the melanoma cells from the subject compared to a control sample of non-melanoma cells.

Various techniques are known to a person of ordinary skill in the art to determine the level of mRNA in a sample. Non-limiting examples of such techniques include microarray analysis, real-time polymerase chain reaction (PCR), Northern blot, in situ hybridization, solution hybridization, or quantitative reverse transcription PCR (qRT-PCR). Methods of carrying out these techniques are routine in the art. Additional methods of determining the level of mRNA in a sample are also well known to a person of ordinary skill in the art and such embodiments are within the purview of the invention.

Various techniques are known to a person of ordinary skill in the art to determine the level of PKC-ζ and/or PKC-ι protein in a sample. Non-limiting examples of such techniques include protein array analysis, Western blot analysis, enzyme-linked immunosorbent assay (ELISA), radio-immune assay (MA), etc. Methods of carrying out these techniques are routine in the art. Additional methods of determining the level of PKC-ζ and/or PKC-ι protein in a sample are also known to a person of ordinary skill in the art and such embodiments are within the purview of the invention.

Similarly, various techniques are known to a person of ordinary skill in the art to determine the activity of PKC-ζ and/or PKC-ι protein in a sample. Methods of carrying out activity assays of PKC-ζ and/or PKC-ι protein are known in the art and are within the purview of the invention.

A reference value corresponding to the level of mRNA or protein for PKC-ζ and/or PKC-ι indicates the level of mRNA or protein for PKC-ζ and/or PKC-ι in the melanoma cells of a subject that is responsive or non-responsive to a melanoma therapy with an inhibitor of PKC-ζ and/or PKC-ι. As such, a reference value corresponding to the level of mRNA or protein for PKC-ζ and/or PKC-ι may be indicative of the subject being responsive or non-responsive to a melanoma therapy with an inhibitor of PKC-ζ and/or PKC-ι.

To practice the methods of the subject invention described herein for identifying a subject as being responsive or non-responsive to a melanoma therapy with an inhibitor of PKC-ζ and/or PKC-ι, a control sample can be one or more of the following:

a) melanocytes from an individual belonging to the same species as the subject and not having melanoma, b) melanocytes from the subject prior to getting melanoma, c) melanocytes from the subject not affected by melanoma, d) melanoma cells from an individual known to be responsive to a melanoma therapy with an inhibitor of PKC-ζ and/or PKC-ι, or e) melanoma cells from an individual known to be non-responsive to a melanoma therapy with an inhibitor of PKC-ζ and/or PKC-ι.

Additional examples of control samples that can be used in the invention can be designed by a person of ordinary skill in the art and such embodiments are within the purview of the invention.

In certain embodiments, the subject used in the invention is a mammal. Non-limiting examples of mammals include human, ape, canine, pig, bovine, rodent, or feline.

Once a subject is identified as being responsive to a melanoma treatment with an inhibitor of PKC-ζ and/or PKC-ι based on the methods of the subject invention, the steps of treating and/or managing melanoma include administering to the subject one or more inhibitors of PKC-ζ and/or PKC-ι described herein.

In preferred embodiments, a melanoma treatment with an inhibitor of PKC-ζ and/or PKC-ι is administered to the subject in combination with one or more additional melanoma therapies. Such additional melanoma therapies can be therapies that do not inhibit PKC-ζ and/or PKC-ι, a surgery, a radiation therapy, an immunotherapy or a combination thereof.

In other preferred embodiments, two inhibitors of inhibitor of PKC-ζ and/or PKC-ι are administered to the subject in combination. In further preferred embodiments, the two inhibitors of PKC-ζ and/or PKC-ι that are administered to the subject in combination are administered in a way that each inhibitor is administered at a sub-therapeutic level.

Once a subject is identified as being non-responsive to a melanoma treatment with an inhibitor of PKC-ζ and/or PKC-ι based on the methods described herein, the step of treating and/or managing melanoma includes administering to the subject one or more melanoma therapies other than an inhibitor of PKC-ζ and/or PKC-ι. Examples of melanoma therapies other than an inhibitor of PKC-ζ and/or PKC-ι include a surgery, a radiation therapy, an immunotherapy or a combination thereof.

In specific preferred embodiments, the subject invention provides a novel atypical PKC inhibitor that is specific to PKC-ι. In further preferred embodiments, the novel atypical PKC inhibitor specific to PKC-ζ is 8-hydroxy-1, 3,6-naphthalenetrisulfonic acid (ζ-Stat). Advantageously, the novel PKC-ζ specific inhibitor can decrease the levels of total and phosphorylated PKC-ζ without affecting PKC-ι. In preferred embodiments of the subject invention, the PKC-ζ specific inhibitor ζ-Stat inhibits cellular signaling pathways that are involved in endothelial-to-mesenchymal transition (EMT) of melanoma cells. Further advantageously, the PKC-ζ specific inhibitor 8-hydroxy-1, 3,6-naphthalenetrisulfonic acid (ζ-Stat) effectively suppresses PKC-ζ mediated EMT and induces apoptosis in melanoma cells.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLES

EXAMPLE 1: Materials

ACPD (Product #: R42691 1) was purchased from Sigma Aldrich (St. Louis, Mo.) and DNDA was obtained from the National Institute of Health—NIH (Bethesda, JVID). They were dissolved in sterile distilled water (vehicle) before use. ζ-Stat was obtained from the National Institute of Health—NIH (Bethesda, Md.). They were dissolved in sterile distilled water (vehicle) before use. PKC-ι (Catalog #610175, 0.25 μg/mL) and Bcl-2 (Catalog #610538, 0.5 μg/mL) antibodies were purchased from BD Biosciences (San Jose, Calif.). PKC-ζ (Catalog # sc-17781, 0.2 μg/mL), NF-kB p65 (Catalog # sc-372-G, 0.2 μg/mL) and Caspase-3 (Catalog # sc-7272, 0.4 μg/mL) antibodies was purchased from Santa Cruz Biotech (Santa Cruz, Calif.). The antibodies to phospho PKC-ζ (Thr 410) (Catalog # PAS-17837, 0.4 μg/mL), Phospho PKC-ι (Thr 555) (Catalog #44-968G, 0.4 μg/mL), E-Cadherin (Catalog #701134, 0.25 μg/mL) and Vimentin (Catalog # MA3-745, 0.25 μg/mL) antibodies were purchased from Thermo Fisher Scientific (Waltham, Mass.). PARP (Catalog #9532, 0.15 μg/mL) and cleaved-PARP (Catalog #9185, 0.15 μg/mL) antibodies were purchased from Cell Signaling (Danvers, Mass.). β-actin-peroxidase (Catalog # A3854, 0.1 μg/mL) antibody was purchased from Sigma (St. Louis, Mo.). CD44 (Catalog # ab51037, 0.2 μg/mL) and β-catenin (Catalog # ab16051, 0.2 μg/mL) antibodies were purchased from Abcam (Cambridge, UK).

Enhanced chemiluminescence (Supersignal West Pico Chemiluminescent Substrate) solution (product #: 34080) was purchased from Pierce (Rockford, Ill.). Dulbecco's phosphate buffered saline without Mg2+ and Ca2+ (DPBS) (product #: D8537) and Trypsin-EDTA (Ethylenediaminetetraacetic acid) solution (product #: T4049) was purchased from Sigma Aldrich (St. Louis, Mo.). WST-1 reagent for cell proliferation, viability and cytotoxicity (catalog #: 11644807001) was purchased from Roche Diagnostics (Mannheim, Germany).

EXAMPLE 2: Database Preparation and Molecular Docking

Database preparation were performed using the National Cancer Institute/Developmental Therapeutics Program (NCI/DTP) and molecular docking was performed by selecting structural pockets in PKC-ι and PKC-ζ proteins which may have the potential of having interactions with small drug like molecules. The detailed procedure was performed as described [35].

EXAMPLE 3: Cell Culture, Media, Cell Lines and Culture Conditions

PCS-200-013 normal melanocyte (derived from the epidermis-basal layer) and SK-MEL-2 metastasized melanoma cell lines (skin derived tissue from metastasis on skin of thigh of a 60 years old Caucasian male). MeWo, was derived from a skin metastasis to the lymph node of a 78 years old Caucasian male. All 3 cell lines were purchased from American Type Tissue Culture Collection (ATCC; Rockville, Md.). Both cell lines were cultured at 37° C. with 5% $CO_2$.

Dermal cell basal medium and the growth kit for normal human melanocytes were also obtained from the ATCC. PCS-200-013 cells were seeded and grown as monolayers in 25 $cm^2$ flasks in low serum (less than 1.0% FBS) conditions in the absence of cholera toxin and phorbol 12-myristate 13-acetate (PMA). The medium contained rh-Insulin (5 μg/mL), Ascorbic Acid (50 μg/mL), L-Glutamine (6 mM), Epinephrine (1.0 mM), Calcium Chloride (1.5 mM), Penicillin (5 μg/mL), Peptide Growth Factor and M8 supplement as proprietary formulations. SK-MEL-2 and MeWo cells were seeded and grown as monolayers in 25 $cm^2$ flasks containing Eagle's minimum essential media—EMEM (90% v/v), fetal bovine serum-FBS (10% v/v) and Penicillin (5 μg/mL). Peptide Growth Factor and M8 supplement as proprietary formulations. SK-MEL-2 and MeWo cells were seeded and grown as monolayers in 25 $cm^2$ or 75 $cm^2$ flasks containing Eagle's minimum essential media—EMEM (90% v/v), fetal bovine serum-FBS (10% v/v) and Penicillin (5 μg/mL).

EXAMPLE 4: Growth Inhibition Assays

For the growth inhibition assays, the PCS-200-013 cells or SK-MEL-2 cells were seeded at 40,000 cells/well into 6-well-plates and treated with the respective inhibitor. Cells in each well were counted after 24 h from the time of treating with the inhibitor at the desired concentration. Each inhibitor had triplicate plates which were counted at $24^{th}$, $48^{th}$ and $72^{nd}$ hours after initiating the inhibitor treatment. Inhibitors were added after 24 h of seeding point. The inhibitor concentrations were none (control), 50 nM, 100 nM, 200 nM, 500 nM and 1 μM. The cells were counted using a hemocytometer. The same procedure was followed for inhibitors ICA-1, ACPD, 3,4-diamino-2,7-naphthalenedisulfonic acid DNDA and 8-hydroxy-1, 3,6-naphthalenetrisulfonic acid (ζ-Stat).

EXAMPLE 5: Wound-Healing, Migration and Invasion Assays

For the wound-healing assay, melanoma cells were seeded into 35 mm dishes in 6-well-plates. After the cells had reached 100% confluency, the wound-healing assay was performed with a sterile pipette tip (1-10 μL pipette tip) by making a scratch through the confluent monolayer. Subsequently, the cells were washed with DPBS and fresh medium (EMEM) was added to each well and the desired amount of inhibitor was added in order to achieve the final concentrations of 50 nM, 100 nM, 200 nM, 500 nM and 1 μM against the control. Cells were cultured for 48 h. In 24 hours intervals, pictures of wound closure were taken and the percentage of wound closure was calculated in three randomly chosen fields.

For the transwell migration and invasion assays, approximately $2 \times 10^5$ melanoma cells in serum-free medium were placed in the upper chamber of the insert with (invasion assay) or without (migration assay) Matrigel (BD Biosciences, San Jose, Calif.). Cells were treated with atypical PKC inhibitors to the upper chamber to achieve the final concentrations of 50 nM, 100 nM, 200 nM, 500 nM and 1 μM against the control. After 72 h incubation at 37° C., the cells remaining in the upper chamber or on the upper surface of the membrane were removed with a cotton swab. After staining with the suitable color reagent, the number of cells that adhered to the underside of the membrane was counted in three randomly chosen fields. Each experiment was performed in triplicate.

The same procedure was followed for inhibitors ICA-1, ACPD, 3,4-diamino-2,7-naphthalenedisulfonic acid DNDA and 8-hydroxy-1, 3,6-naphthalenetrisulfonic acid (ζ-Stat).

EXAMPLE 6: Cell Fractionation, Immunoprecipitation and Western Blot Analysis Approximately $2 \times 10^5$ cells from PCS-200-013 and SK-MEL-2 cell lines were plated in T25 flasks until they become 70% confluent. Confluent cells were semi-synchronized by contact inhibition and serum starvation for 48 hrs. Subsequently, cells were incubated with serum and atypical inhibitors. The cells were removed at specific times and were placed in ice to terminate the incubation. Cells were washed at least two times with ice cold DPBS. Cells were then scrapped, re-suspended and sonicated in 500 μL of homogenization buffer (50 mM HEPES—pH 7.5), 150 mM NaCl, 0.1% Triton X, 1 mM EDTA (ethylenediaminetetraacetic acid), 2 mM EGTA [glycol-bis (2-aminoethylether)-N, N, N',N'-tetraacetic acid], 0.1 mM orthovanadate, 1 mM NaF, 2 mM PMSF (phenylmethylsulphonylfluoride), 1 mM DTT (dithiothreitol) and 0.15 U/mL aprotinin. Cell suspensions was then sonicated and centrifuged at 100,000 g for 30 minutes. The protein concentrations was determined using Bradford method. Subsequently, approximately 800 μg of proteins were immunoprecipitated with the antibody against desired protein. In some cases cell lysates were suspended with anti-HFS-1 antibody, rocking overnight at 4° C. Agarose beds were added after 24 hrs. Then the complex of cell lysate-anti HSF-1 antibody-agarose beads was rocked at 4° C. for 2 hrs. After washing the beads, approximately 60 of the sample loading buffer was added to dissolve all the protein on the beads. Proteins were then separated on sodium dodecyl sulfate polyacrylamide gel electrophoresis (SDS-PAGE) and transblotted followed by immunoblotting with anti-PKC-ζ or anti-PKC-ι or anti-HSF-1 antibody or phosphospecific antibodies. Immunoreactive bands were visualized with enhanced chemiluminescence.

EXAMPLE 7: PKC Activity Assay

PKC activity assay was conducted by monitoring the phosphorylation of myelin basic protein (MBP), a known substrate for PKCs. The detailed procedure was performed as described in Ling, D. S. F. et al. (2002) for PKC-ι and PKM-ζ [37].

PKC activity assay was performed by suspending 0.5 µg of PKC-ζ and PKC-ι separately in 200 µL of PKC kinase buffer to test the ability of PKC-ζ and PKC-ι of phosphorylating and immunoprecipitating HSF-1 of the SK-MEL-2 cells and PCS-200-013 cells. The PKC kinase buffer composition was 20 mM Tris-HCL (pH of 7.5), 6 mM Magnesium acetate, phosphotidylserine (5 µg, 20 µL of 10 mg/mL solution), ATP (0.0045 mg/mL) and also the desired inhibitors, wherever appropriate (ICA-1, ACPD, DNDA and ζ-Stat). The inhibitor was used in two different concentrations as 1 µM and 0.5 µM. The reaction was terminated after incubation for 5 minutes at 30° C. by addition of sample loading buffer. Samples were then separated by PAGE and immunoblotted against anti-PKC antibodies (either PKC-ι or PKC-ζ) and against phosphospecific HSF-1 antibodies. Samples were also probed against anti-HSF-1 antibody to determine that the protein immunoprecipitaed was HSF-1. The signal was visualized using enhanced chemiluminescence.

The same procedure was followed for inhibitors ICA-1, ACPD, 3,4-diamino-2,7-naphthalenedisulfonic acid (DNDA) and 8-hydroxy-1, 3,6-naphthalenetrisulfonic acid (ζ-Stat).

EXAMPLE 8: Inhibitor Dose Response Curves

Dose curves (inhibitor concentrations vs cell population after 3 days) for ICA-1, ACPD, DND and ζ-Stat were obtained for all 3 cell lines as follows. PCS-200-013, SK-MEL-2 and MeWo cells ($4 \times 10^4$) were cultured in 25 cm$^2$ flasks and treated with either equal volume of sterile water (vehicle control). Cells were treated every 24 h during 3 day incubation period and cells were then lifted using Trypsin-EDTA solution (1.5 mL/flask) and neutralized with the equal volume of media. Subsequently, live cells were counted using the Scepter, an automated cell counter from Millipore (Billerica, Mass.). The cell growth inhibition for all inhibitors for the two malignant cell lines (SK-MEL-2 and MeWo) were quantified by counting the viable cells at 24 hour intervals. Cell counts obtained from Scepter was compared with the counts obtained from the Cellometer Vision from Nexcelom Bioscience (Lawrence, Mass.).

EXAMPLE 9: Immunofluorescence

Approximately 75,000 cells were plated in a glass chamber slide. After 24 h post plating period, cells were washed 3 times with ice cold DPBS and were fixed with 1:1 Methanol to Acetone solution for 5 minutes at 20° C. Then, the cells were blocked in 8% normal goat serum for 45 minutes. This was followed by incubation with primary mouse antibody against PKC-ι and PKC-ζ accordingly for 90 minutes and subsequent incubation with anti-mouse secondary antibody for 30 minutes. Fluorescence Isothocyante fluorescing molecules were used for fluorescing PKC-ι and PKC-ζ proteins for 30 minutes. Cells were washed 3 times with DPBS prior to blocking with 8% normal horse serum for 45 minutes. Subsequently, cells were incubated with primary rabbit antibody against HSF-1 for 90 minutes and then incubated with anti-rabbit secondary antibody for 30 minutes. Texas Red fluorescing molecule was used to cause fluorescence of the HSF-1 protein for 30 minutes. Cells were washed three times with DPBS and were observed under Leitz Orthoplan scanning confocal microscope. Cell nuclei were visualized with mounting medium containing DAPI. Images were captured using a CCD camera with the Smart Capture Program. Photographs were taken with the same exposure of each setting for each experiment. To illustrate subcellular regions of protein co-localization, individual red and green stained images derived from the same field were merged and areas of protein co-localization appeared as yellow.

EXAMPLE 10: NMR Experiments for Determining the Degradation of Inhibitors Over Time $^1$H NMR experiments were performed using 500 MHz Varian NMR spectrophotometer. Inhibitor concentration of 50 µM (ACPD, ICA-1, DNDA, and ζ-Stat) were initially maintained in the 5 mL growth media in a T25 flask. This solution was incubated at 37° C. and 5% $CO_2$. Aliquots of 0.5 mL were taken out after 24 hours post incubation period and this was continued for 3 more days. These aliquots were analyzed for the $^1$H NMR spectra of the respective drug to determine the changes in the concentrations compared to the reference spectra.

EXAMPLE 11: WST-1 Assay for Cell Viability and Cytotoxicity

Approximately $4 \times 10^3$ cells (PCS-200-013, SK-MEL-2 and MeWo) were cultured in a 96 well plate. After 24 h post plating time, fresh media were supplied (200 µL/well) and treated with either equal volume of sterile water (vehicle control) or with the half maximal inhibitory concentration ($IC_{50}$) of ICA_1, ACPD, DNDA, or ζ-Stat. This $IC_{50}$ was obtained based on the cell viability counts in the previous experiments. Additional doses of sterile water or inhibitor were supplied every 24 h during 3 day incubation period. At the end of 3 day treatment, media were removed and fresh media (100 µL) were added with 4-[3-(4-iodophenyl)-2-(4-nitropheny))-2H-5-tetrazolio]-1,3-benzene disulfonate (WST-1) reagent (10 µL) to each well. The absorbance was measured at 450 nm for every 0.5 hour up to 3 hours using the Synergy HT microplate reader from Biotek (Winooski, Vt.).

EXAMPLE 12: Statistical Analysis

All data are presented as mean±SD. Statistical analysis was performed with one or two-way ANOVA followed by Tukey HSD test as multiple comparisons tests using the "VassarStats" web tool for statistical analysis developed by Dr. Richard Lowry, PhD. P-value≤0.05 or ≤0.01 was considered to indicate statistical significance.

EXAMPLE 13: Specific Binding of ACPD and DNDA to aPKCs

Figure 1D:
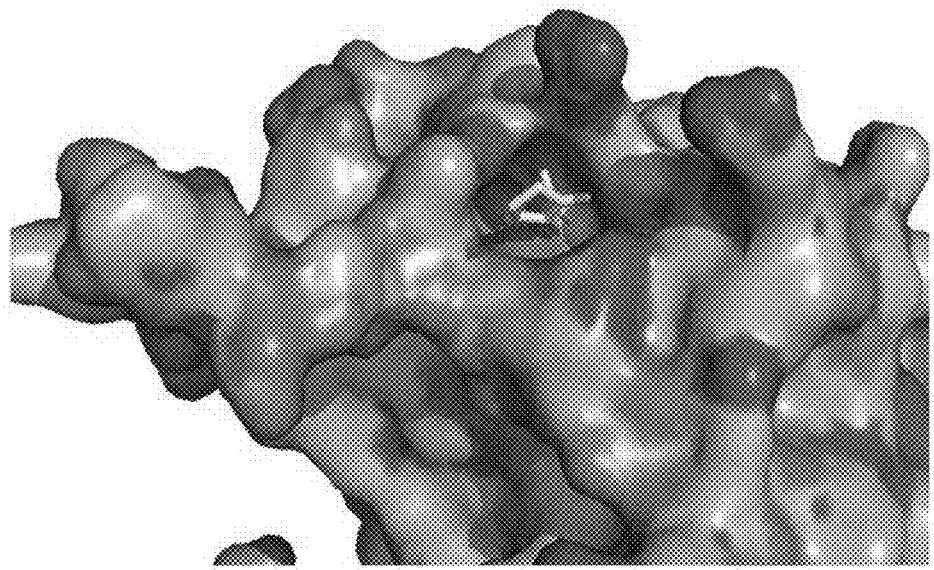
FIG. 1D shows an image depicting the molecular docking of ACPD on PKC-ζ.
Figure 1E:
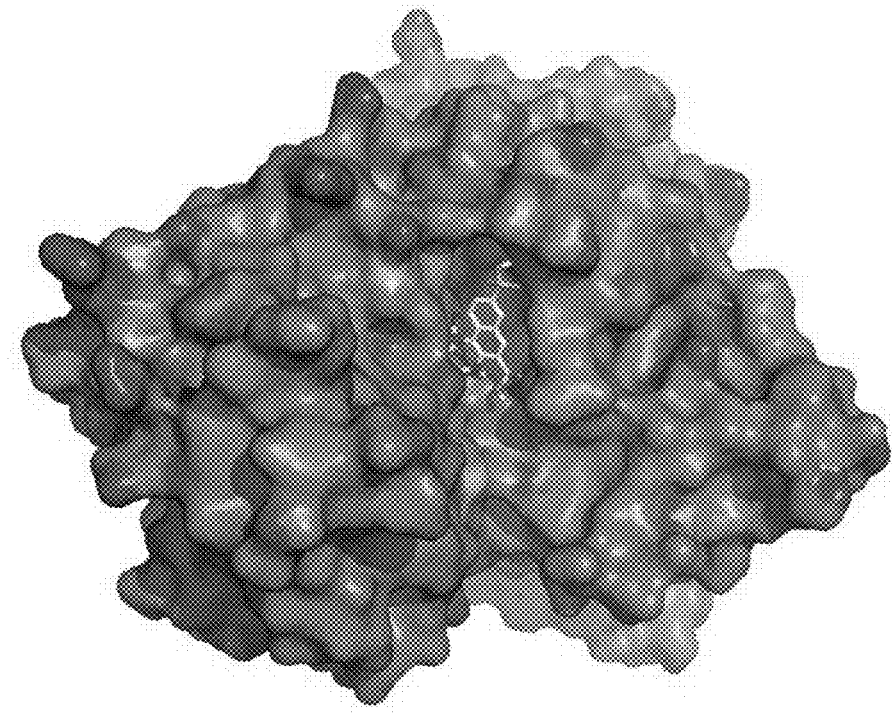
FIG. 1E shows an image depicting the molecular docking of DNDA on PKC-ι.
Figure 1F:
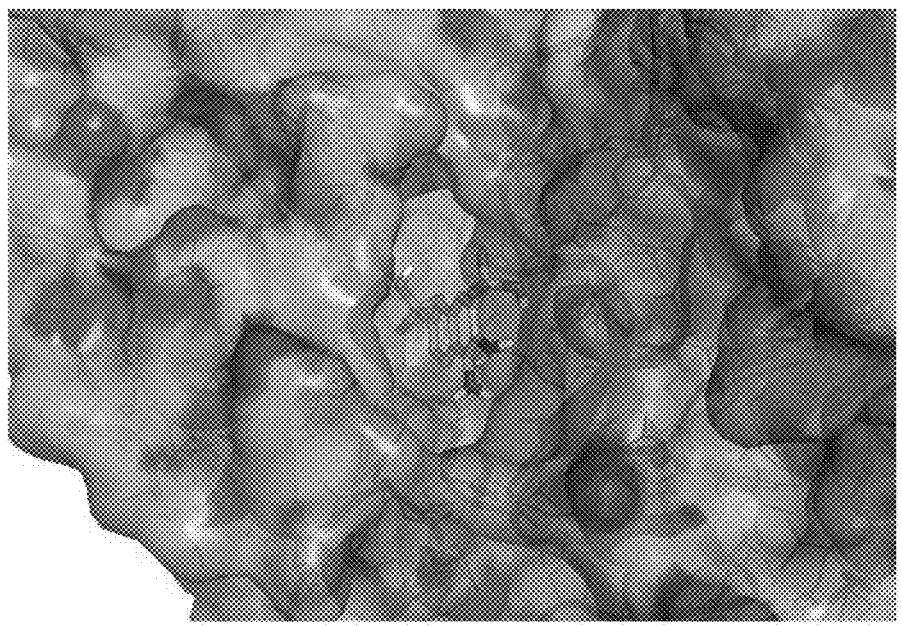
FIG. 1F shows an image depicting the molecular docking of DNDA on PKC-ζ.

To establish the therapeutic potential of atypical PKCs, ACPD (FIG. 1A) and DNDA (FIG. 1 B) were identified based on the molecular docking (MD). Approximately 3×10⁵ drug like organic compounds (molecular weight <500 g/mol) in NCI/DTP, were screened by positioning them in the structural pockets of PKC-ι and PKC-ζ and then scored based on predicted polar and non-polar interactions. ACPD was found to interact with amino acid residues Gin 469, Ile 470, Lys 485 and Leu 488 of the catalytic domain of PKC-ι (FIG. 1C) and Arg 265, Pro 267, Asp 269 and Lys 290 of the catalytic domain of PKC-ζ (FIG. 1D). DNDA interacts with amino acid residues of Asp 339, Asp 382, Leu 385 and Thr 395 of the catalytic domain of PKC-ι (FIG. 1E) and Asp 337, Asp 380, Leu 383 and Thr 393 of the catalytic domain of PKC-ζ (FIG. 1F).

EXAMPLE 14: Specificities of ACPD and DNDA Based on Activity Assays

Determination of specific activity of inhibitors was essential since 84% similarity is observed in the primary structures of the PKC-ι and PKC- catalytic domains. Specificity of ACPD was previously reported as inhibiting both PKC-ι, approximately 40% at 10 1M, and PKC-ζ, about 60% at 10 μM, without affecting other PKC isoforms [24]. Additionally, ACPD does not inhibit other kinases such as MAPK, Akt2, FGFR 1/2/3/4, mTOR, GSK3B, IRAK1/4, JAK 1/2, MEK1, ERK1/2, JNK 1/2, PKA, Src, ROCK2 and PI3K [25, 26].

Figure 2:
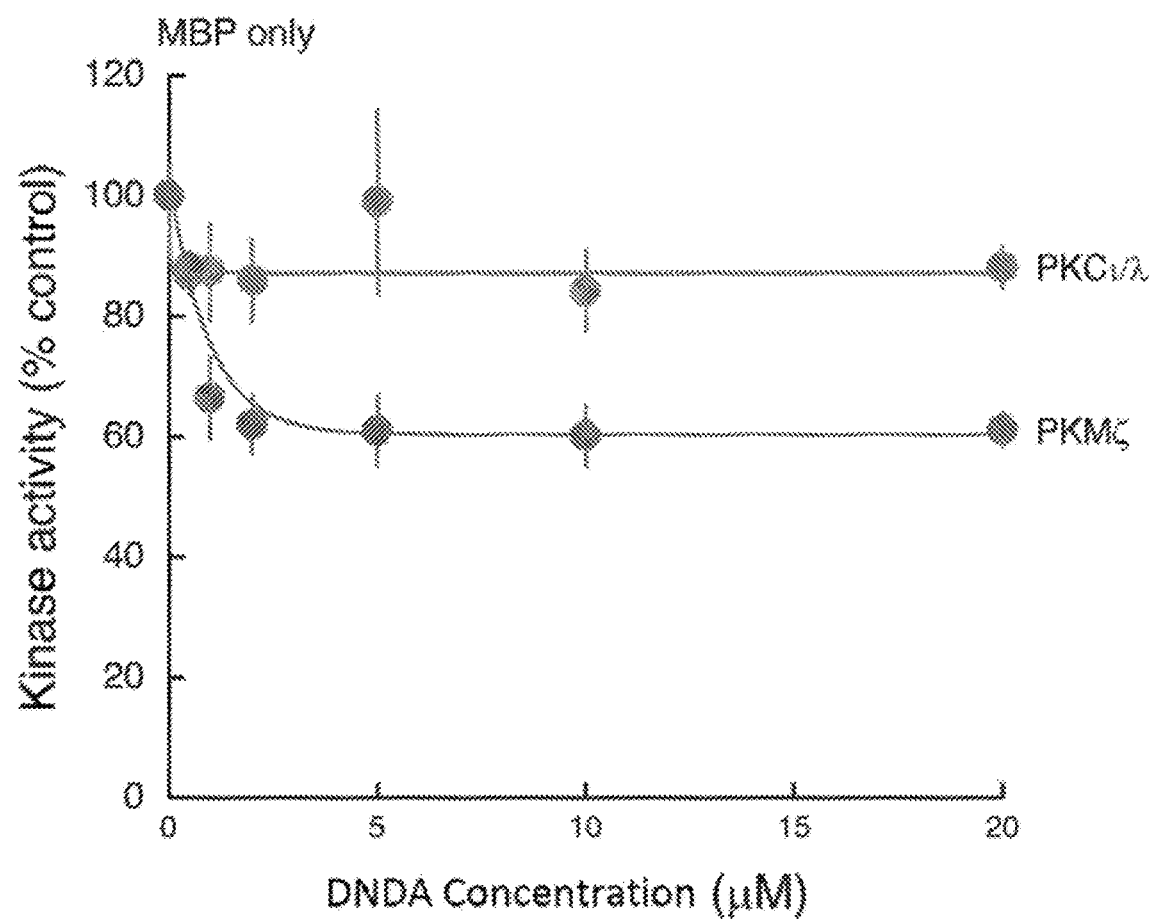
FIG. 2 shows the effect of DNDA as specifically inhibiting PKC-ι and/or PKM-ζ.
Figure 3A:
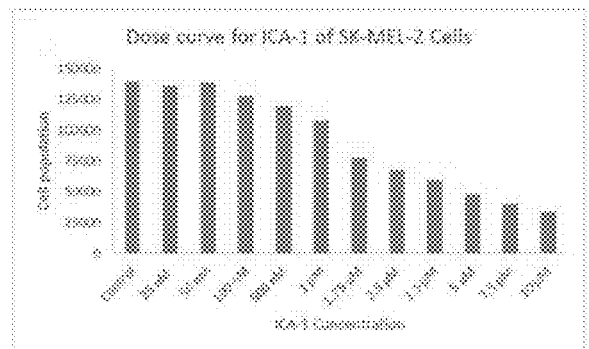
FIG. 3A shows a dose response curve for ICA-1 for SK-MEL-2 cells.
Figure 3B:
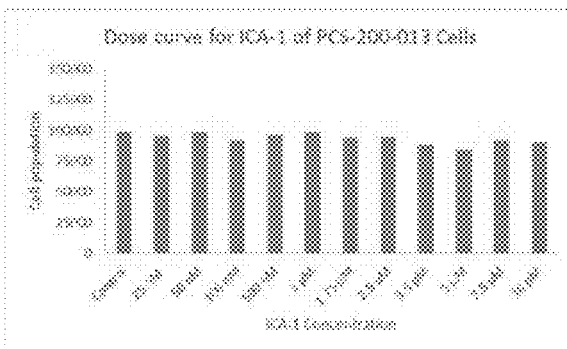
FIG. 3B shows a dose response curve for ICA-1 for PCS-200-013 cells.
Figure 3C:
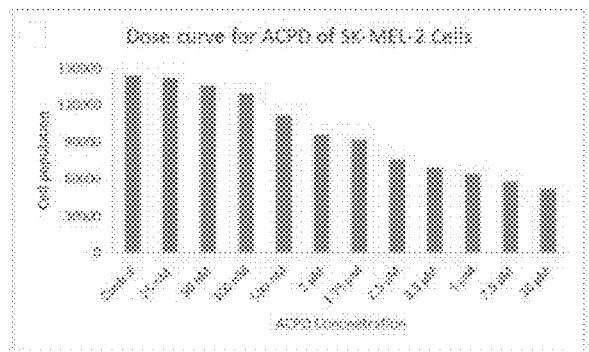
FIG. 3C shows a dose response curve for ACPD for SK-MEL-2 cells.
Figure 3D:
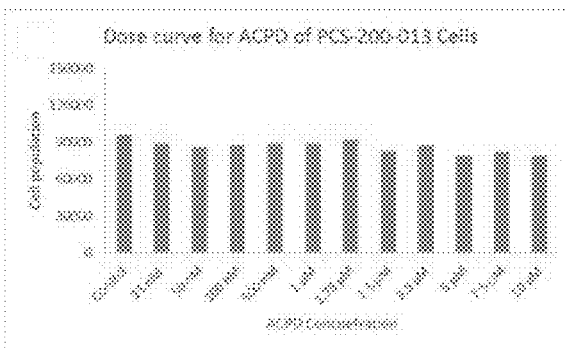
FIG. 3D shows a dose response curve for ACPD for PCS-200-013 cells.
Figure 4A:
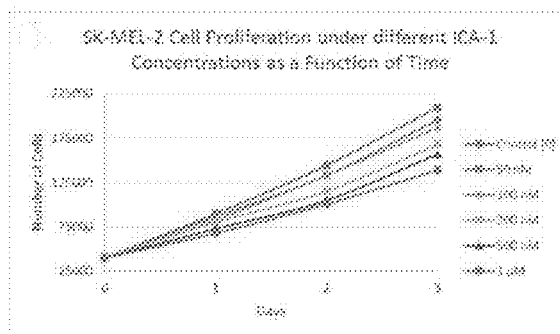
FIG. 4A shows cell proliferation of SK-MEL cells in the absence and presence of different concentrations of ICA-1.
Figure 4B:
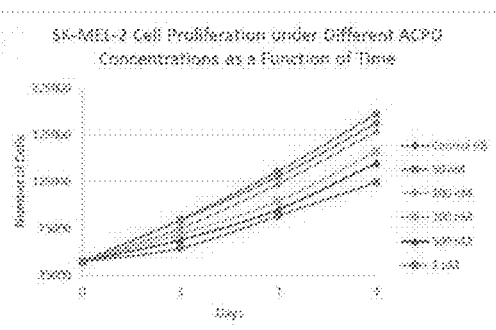
FIG. 4B shows cell proliferation of SK-MEL cells in the absence and presence of different concentrations of ACPD.

The activity of DNDA (FIG. 2) was determined for a series of concentrations (0-20 μM) using recombinant active PKC-ι or PKM-ζ in the presence of MBP (5 μg). The maximum inhibition of PKC-ζ was 40% and reached at 2 (P≤0.05). Inhibition remained the same upon increasing the concentration PKM-ζ is an active form of PKC-ζ found in human brain due to proteolytic cleavage of N-regulatory domain and the C-terminal catalytic domain of PKC-ζ [27-29]. The maximum inhibition of PKC-ι was approximately 15% and reached at 0.5 μM (P≤0.05) concentration.

EXAMPLE 15: Dose Curves for PKC-ι and PKC-ζ

Cell growth of malignant melanoma cells was reduced by applying PKC-ι and PKC-ζ inhibitors (FIGS. 3A-3D and 4A-4B). Both PKC-ι, and PKC-ζ heavily contributed to the migration of metastasized melanoma cells and migration can be suppressed using ICA-1 and ACPD. For example, Tables 1-2 provide a summary of the percentage inhibition of growth of SK-MEL-2 cells (Table 1 for ICA-1 and Table 2 for ACPD) as a function of time over 72 h period. Both ACPD and ICA-1 have 40% effectiveness on cell proliferation inhibition at the highest concentration used. Inhibition is increased upon increasing the concentration.

TABLE 1

Growth inhibition by ICA-1.

| ICA-1 Concentration | % Inhibition | | |
|---|---|---|---|
| | Day 1 | Day 2 | Day 3 |
| 0 (Control) | 0 | 0 | 0 |
| 50 nM | 4 | 8 | 7 |
| 100 nM | 8 | 8 | 11 |
| 200 nM | 11 | 20 | 20 |
| 500 nM | 19 | 27 | 25 |
| 1 μM | 25 | 30 | 34 |

TABLE 2

Growth inhibition using ACPD.

| ACPD Concentration | % Inhibition | | |
|---|---|---|---|
| | Day 1 | Day 2 | Day 3 |
| 0 (Control) | 0 | 0 | 0 |
| 50 nM | 1 | 4 | 5 |
| 100 nM | 11 | 10 | 9 |
| 200 nM | 19 | 23 | 20 |
| 500 nM | 26 | 30 | 26 |
| 1 μM | 36 | 35 | 37 |

EXAMPLE 16: Inhibitor dose response curves.

Figure 5E:
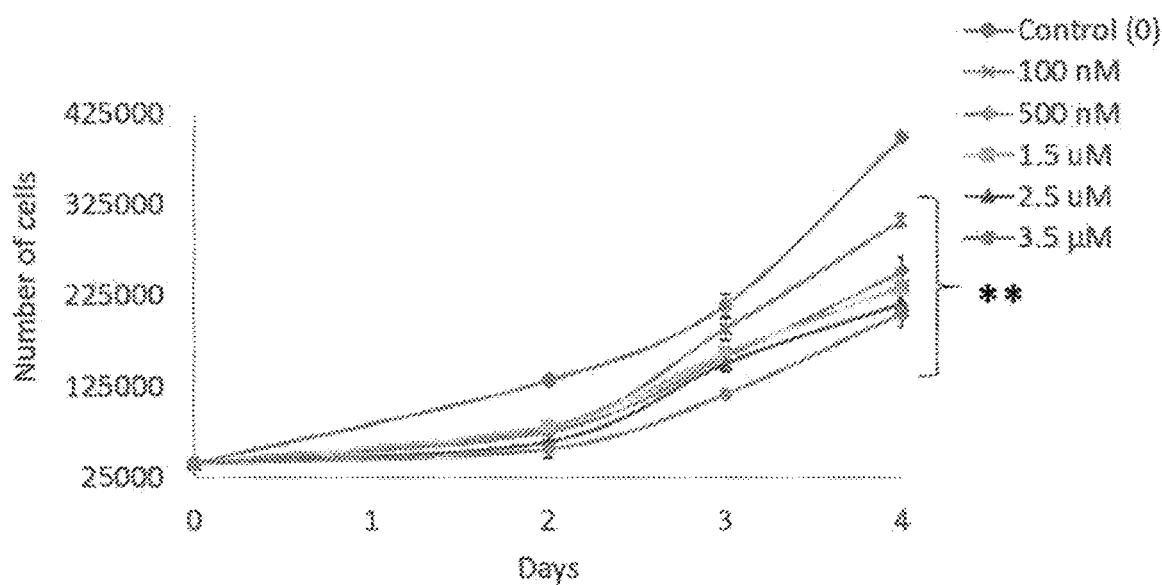
FIG. 5E shows the effect of DNDA on MeWo cell number.

Dose curves for ACPD and DNDA were obtained to investigate the effect on cell proliferation of normal and malignant cell lines over a wide range of concentrations. ACPD and DNDA did not show a significant effect on PCS-200-013 (FIG. 5A), except 3.5 μM DNDA, at which concentration a 13.5% inhibition was achieved (p≤0.05). Both inhibitors significantly decreased cell proliferation of SK-MEL-2 and MeWo cells upon increasing the concentrations. ACPD decreased proliferation by 20% for 1.5 μM (p≤0.01), 48% for 2.5 μM (p≤0.01) and 51% for 3.5 μM (p≤0.001)(FIG. 5B). DNDA decreased by 17% for 500 nM (p≤0.01), 24% for 1.5 μM(p≤0.01), 52%) for 2.5 1M (p≤0.01) and 57 for 3.5 μM (p≤0.01)(FIG. 5C) in SK-MEL-2 cells. ACPD decreased proliferation by 28% for 500 nM (p≤0.01), 41% for 1.5 μM (p≤0.01), 54% for 2.5 1M (p≤0.01) and 58% for 3.5 μM (p≤0.01) (FIG. 5D). DNDA decreased proliferation by 37% for 500 nM (p≤0.01), 41% for 1.5 μM (p≤0.01), 46% for 2.5 μM (p≤0.01) and 48% for 3.5 μM (p≤0.01) (FIG. 5E) in the MeWo cells. These results suggest that both inhibitors can effectively decrease the cell population while not having a significant effect on normal melanocytes. Based on these results, the half maximal inhibitory concentration ($IC_{50}$) of both ACPD and DNDA was found to be approximately 2.5 μM and this value was used in later experiments.

EXAMPLE 17: WST-1 assay for cell viability and cytotoxicity.

Figure 6C:
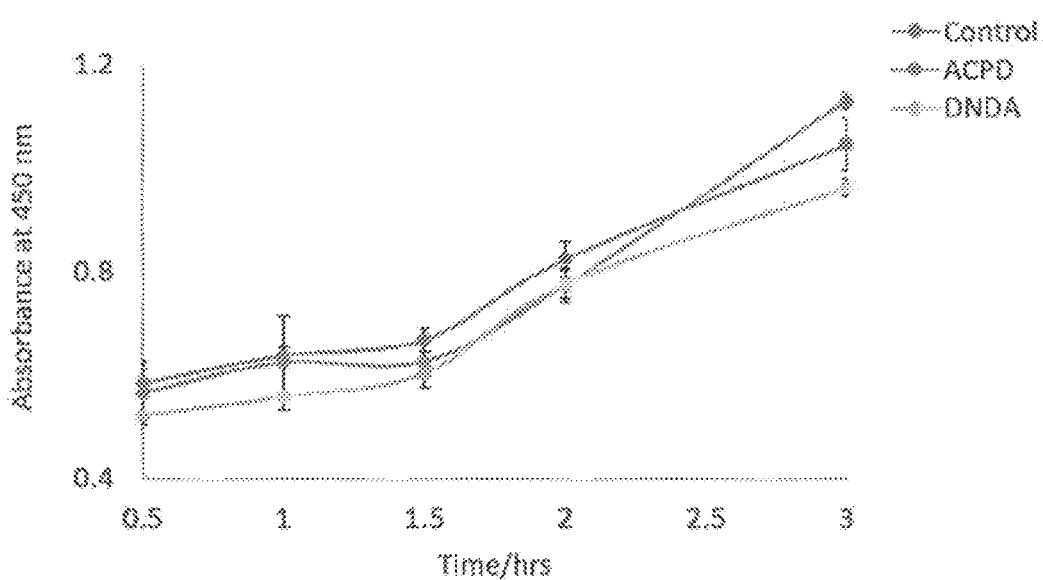
FIG. 6C shows cell proliferation was measured using the WST-1 assay for MeWo cells.

WST-1 assay was performed to determine the in-vitro cytotoxicity of ACPD and DNDA on normal and malignant cell lines. Measured absorbance at 450 nm is directly proportional to the number of cells present. Cells produce a water soluble formazan with WST-1 as a result of their mitochondrial dehydrogenase activity. WST-1 assay is preferred over 3-(4,S-Dimethyl-2-thiazolyl)-2, 5-diphenyl-2Htetrazolium bromide (MTT) test since MTT needs to add acidic isopropanol to dissolve formazan which gives an additional toxicity to cells [30]. Both inhibitors did not show a significant effect on normal cells (FIG. 6A). ACPD did not show a significant effect on either malignant cells, but DNDA showed a significant decrease in absorption (p≤0.05) on SK-MEL-2 (FIGS. 6B and 6C).

EXAMPLE 18: Wound healing assay for ACPD and ICA-1.

The results of a wound healing assay are provided in FIGS. 7A-7B. In control samples, the scratch was completely covered in two days; whereas, the scratch was not completely covered samples treated with both 200 nM and 1 µM concentrations of ICA-1 or ACPD. The scratch was even clearer after two days in 1 µM sample compared to 200 nM sample. Also the number of dead cells floating was highest in 1 µM, followed by 200 nM; whereas, floating cells were rarely observed in the control samples.

EXAMPLE 19: Wound healing assay for ACPD and DNDA.

A wound healing assay was performed to investigate the effect of ACPD and DNDA on malignant melanoma cell migration in vitro. Wound healing assay is commonly used to investigate in vitro migration of cancer cells [31-33]. For the wound-healing assay, melanoma cells were seeded into 35 mm dishes in 6-well-plates. After the cells had reached 100% confluency, the wound-healing assay was performed with a sterile pipette tip (1-10 µL pipette tip) by making a scratch through the confluent monolayer. Subsequently, the cells were washed with DPBS and fresh medium (EMEM) was added to each well and the desired amount of inhibitor was added. Each well was subsequently incubated with sterile water or desired amount of ICA-1, ACPD, DNDA, or c-Stat to achieve the final concentration of the half maximal inhibitory concentration (IC50) for each inhibitor. Plates were incubated at 37° C. and 5% $CO_2$ and photographs of wound closure were taken utilizing a Motic AE31E microscope (40× magnification). The percentage of wound closure was calculated after 3 or 4 days.

Figure 8A:
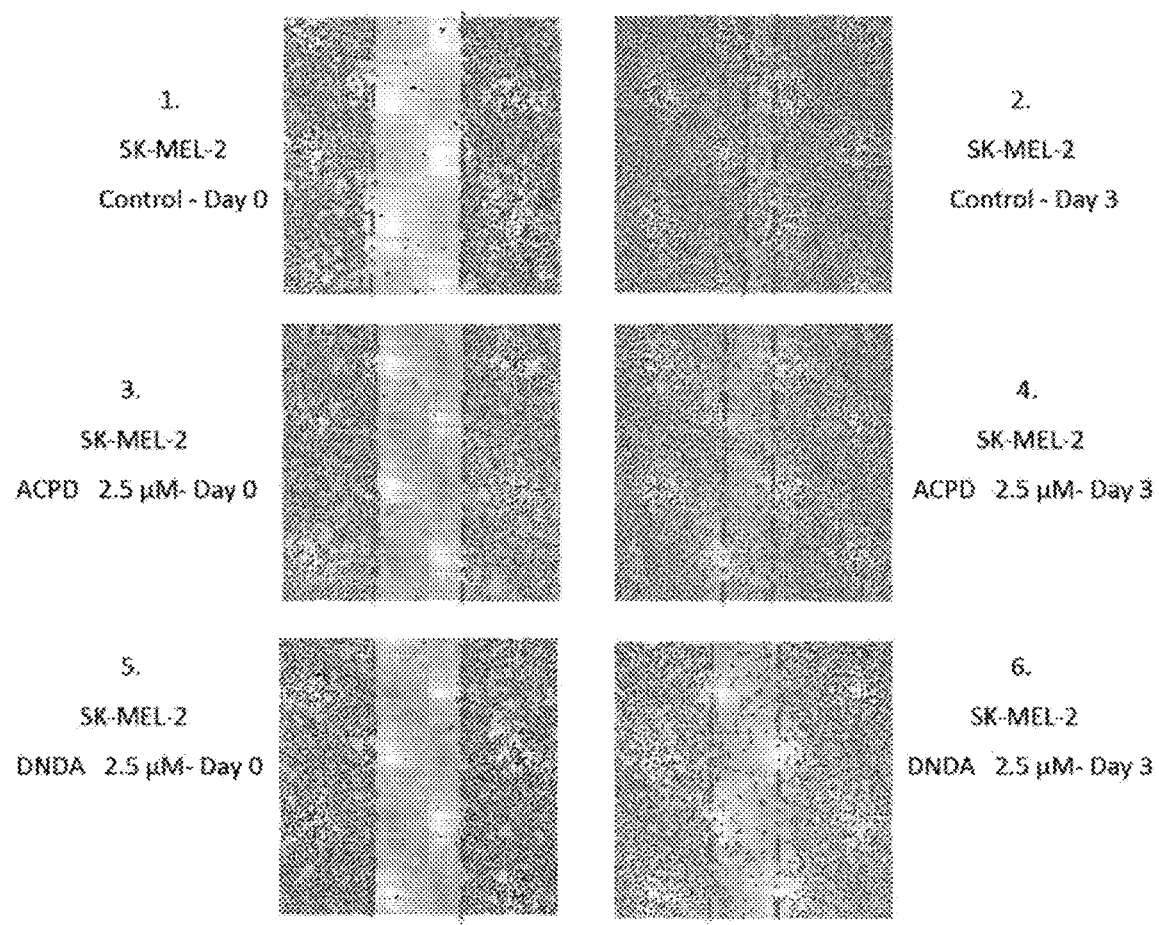
FIG. 8A shows melanoma cell migration measured using a wound healing assay for SK-MEL-2 cells in the absence and presence of ACPD and DNDA.
Figure 8B:
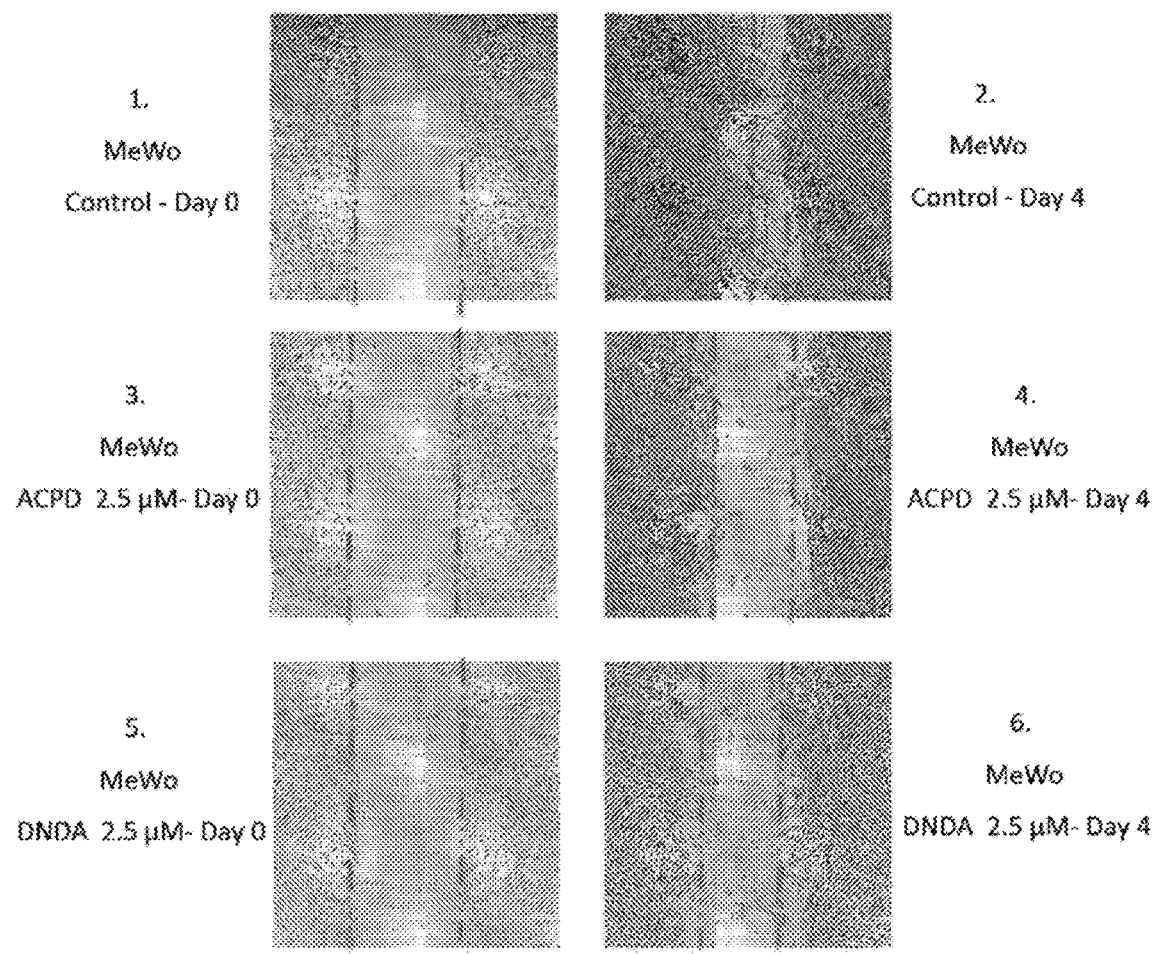
FIG. 8B shows melanoma cell migration measured using a wound healing assay for MeWo cells in the absence and presence of ACPD and DNDA.

In one set of experiments, cells were cultured for 48 h. In 24 hours intervals, pictures of wound closure were taken and the percentage of wound closure was calculated in three randomly chosen fields. FIG. 5A shows photographs for each cell line are compared as "day 0" (starting point) and "day 3" or "day 4" for both malignant ceil lines (FIG. 8A for SK-MEL-2 cells and FIG. 8B for MeWo cells). In each figure, cells treated with ACPD 2.5 µM and DNDA 2.5 µM were compared with their respective controls. The areas of the scratch (wound) were calculated and compared to determine the statistical significance (FIG. 8C). It was found that both inhibitors significantly reduce the wound closure (p≤0.01) of both cell lines. Results suggest that both drugs are equally effective in reducing cell migration in vitro.

EXAMPLE 20: BME Invasion Assay

This invasion assay was performed to investigate the effect of ACPD and DNDA on malignant melanoma cell invasion in vitro. Even though it is similar to the Boyden chamber assay, it avoids scraping off the Matrigel and staining to assess migrated number of cells through filter. Hence, the method carries less human error compared to conventional Boyden chamber assay. Migrated cells were stained with a fluorescent marker, Calcein-AM. Live cells cleave the ester (AM) of the molecule in order to produce fluorescence. Thus, the amount of fluorescence accumulated in the bottom chamber is proportional to the number of invaded cells. The relative fluorescent units (excitation at 485 and emission at 528 nm) after 2 h exposure were reported for inhibitor treatments for both SK-MEL-2 and MeWo cell lines compared to controls (FIG. 8D). Invasion was significantly reduced (p≤0.05) by 24% and 21% in ACPD (2.5 µM) treated SK-MEL-2 and MeWo cells. In DNDA (2.5 µM) treated samples, the invasion was significantly reduced (p≤0.05) by 32% in both SK-MEL-2 and MeWo cells compared to controls.

EXAMPLE 21: Effect of Inhibitors on aPKC Levels in Malignant Melanoma

Figure 9A:
FIG. 9A shows PKC-ι expression in ICA-treated samples.
Figure 9B:
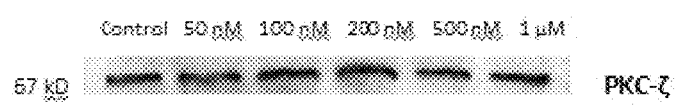
FIG. 9B shows PKC-ζ expression in ICA-treated samples.
Figure 9C:
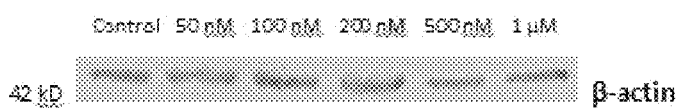
FIG. 9C shows β-actin expression in ICA-treated samples.
Figure 9D:
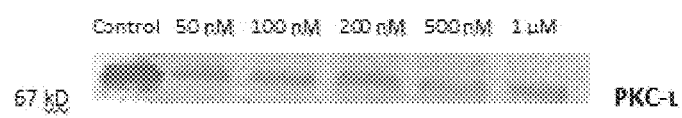
FIG. 9D shows PKC-ι expression in ACPD-treated samples.
Figure 9E:
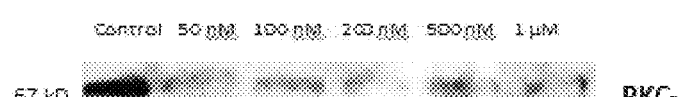
FIG. 9E shows PKC-ζ expression in ACPD-treated samples.
Figure 9F:
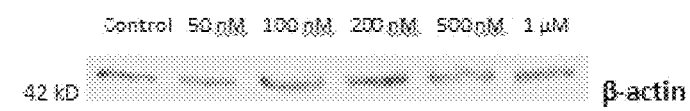
FIG. 9F shows β-actin expression in ACPD-treated samples.

PKC-ι expression was examined in western blot analysis for ICA-1 and ACPD treated samples. ICA-1 treated samples showed a significant decrease of PKC-ι level upon increasing the ICA-1 concentration (FIG. 9A). ACPD also showed good decrease in PKC-ι level upon addition of ACPD compared to control (FIG. 9D). ICA-1 appeared to be more effective compared to ACPD in decreasing PKC-ι in SK-MEL-2 cell line (malignant melanoma). PKC-ζ level was decreased upon treating with ACPD (FIG. 9E) but ICA-1 treated samples did not show an effect of decreasing the levels of PKC-ζ upon increasing ICA-1 (FIG. 9B). This result confirms that ICA-1 is specific only to PKC-ι and ACPD is effective on inhibiting both PKC-ι and PKC-ζ. B-actin was measured in both experiments (ICA-1 and ACPD treatments) as an internal control (FIGS. 9C and 9F).

EXAMPLE 22: Effects of ACPD and DNDA on aPKC and Phospho-aPKC Expression

Western blots (WB) were performed to investigate the effect of ACPD and DNDA on the expression of aPKCs on malignant melanoma. As shown in FIG. 10A, ACPD effectively reduced the PKC-ι level by 43% and by 31% pPKC-ι in SK-MEL-2 cells and by 46%; of PKC-ι and 26% of pPKC-ι in MeWo cells. DNDA decreased the levels of PKC-ι by 52%, pPKC-ι by 33% in SK-MEL-2 cells and by 27% of PKC-ι and pPKC-ι by 20% in MeWo cells.

As shown in FIG. 10B, ACPD effectively reduced the PKC-ζ level by 42% and by 29% of pPKC-ζ in SK-MEL-2 cells and by 42% of PKC-ζ and 23% of pPKC-ζ in MeWo cells. DNDA reduced the levels of PKC-ζ by 33%, pPKC-ζ by only 17% in SK-MEL-2 cells and by 60% of PKC-ζ and pPKC-ζ by 29% in MeWo cells. All values (percent) were calculated compared to their respective control in Western blot. B-actin was used as the internal control to ensure that equal amounts of proteins were loaded in each lane in SDS-PAGE.

EXAMPLE 23: Effect of ACPD and DNDA on Apoptosis of Malignant Melanoma

Figure 11:
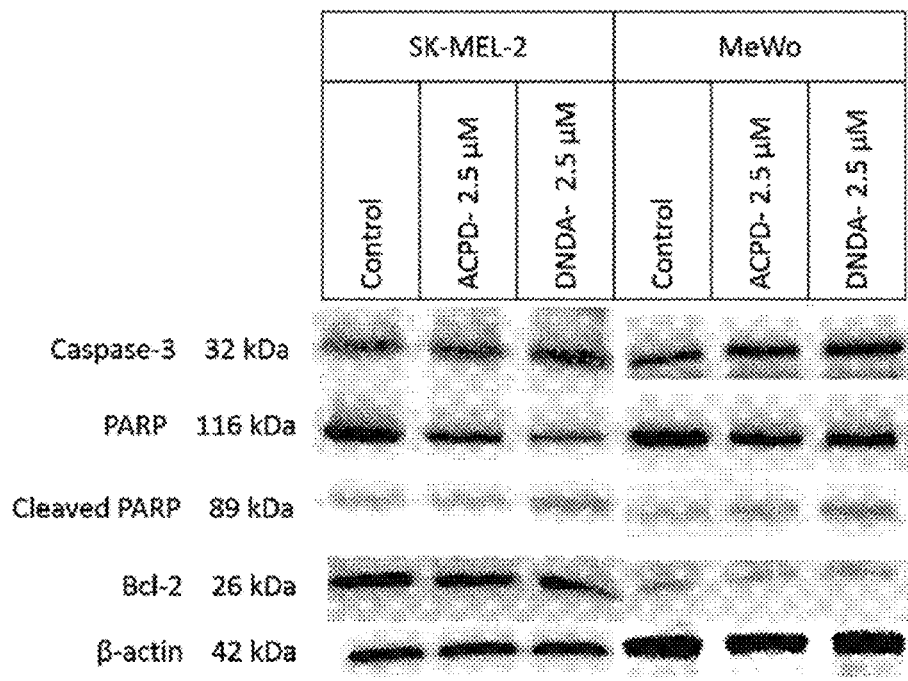
FIG. 11 shows the induction of apoptosis markers Caspase-32, cleaved PARP and Bcl-2 in the absence and presence of aPKC inhibitors ACPD and DNDA in SK-MEL-2 and MeWo cells.

Since both inhibitors effectively inhibit melanoma cell proliferation, the inventors tested the potential of the inhibitors on inducing the apoptosis. As shown in FIG. 11, Caspase-3 levels increased by 26% and 17% in ACPD treated SK-MEL-2 and MeWo cells, respectively. Caspase-3 levels increased by 32% and 39% in DNDA treated SK-MEL-2 and MeWo cells, respectively. Poly ADP-ribose polymerase (PARP) levels decreased by 33% and by 24% in ACPD treated SK-MEL-2 and MeWo cells, respectively, while cleaved PARP levels increased by 14% and 18%, respectively. In DNDA treated samples, PARP levels increased by 12% and by 9% in SK-MEL-2 and MeWo cells, respectively, while cleaved PARP levels increased by 16% and 10%, respectively. Similarly, Bcl-2 levels decreased by 13% and by 25% in ACPD treated SK-MEL-2 and MeWo cells, respectively, while in DNDA treated cells Bcl-2 levels decreased by 7% and by 32% in SK-MEL-2 and MeWo cells, respectively.

EXAMPLE 24: Effect of Inhibitors on EMT

Figure 12:
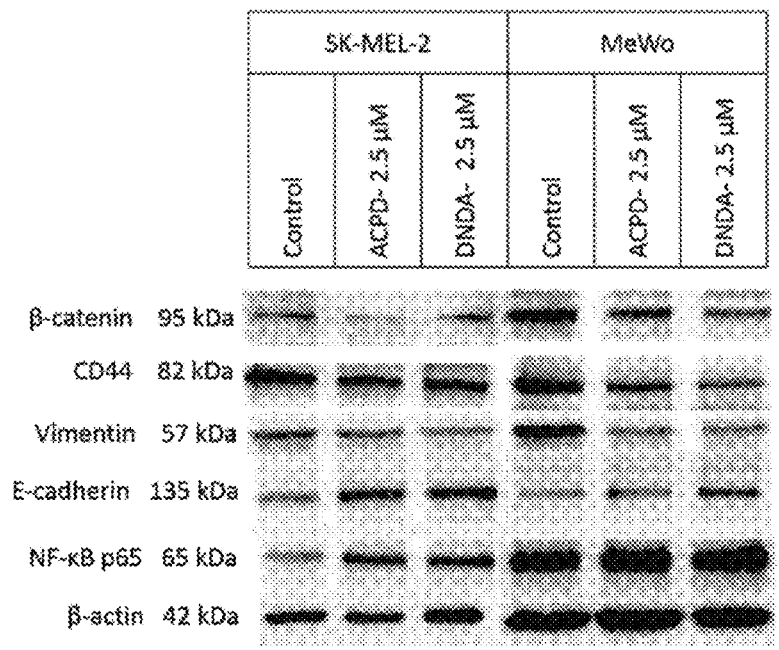
FIG. 12 shows the expression of markers for epithelial-to-mesenchymal transition (EMT) in the absence and presence of aPKC inhibitors ACPD and DNDA in SK-MEL-2 and MeWo cells.

As shown in FIG. 12, the inventors also investigated the effects of ACPD and DNDA on EMT which is an essential step in cancer progression. β-catenin decreased by 39% and 16% in ACPD treated SK-MEL-2 and MeWo cells, respectively, compared to 13% and 21% down regulation in DNDA treated samples. CD44 also decreased by 19% and 34% in ACPD treated SK-MEL-2 and MeWo cells, respectively compared to 27% and 43% down regulation in DNDA treated samples. Vimentin levels decreased by 51% and 38% in ACPD treated SK-MEL-2 and MeWo cells, respectively, compared to 49% and 45% decrease in DNDA treated samples. E-cadherin levels increased by 18% and 35% in ACPD treated SK-MEL-2 and MeWo cells, respectively, compared to 28% and 29% increase in DNDA treated samples. NF-KB p65 levels were also investigated since it has a well-known multi-functional nature in many signal cascades. Interestingly, NF-KB p65 levels increased by 31% and 69% in ACPD treated SK-MEL-2 and MeWo cells, respectively, compared to 49 o and 89% increase in DNDA treated samples.

EXAMPLE 25: Association of PKC-z and Vimentin

PKC-ι and PKC-ζ were immunoprecipitated (IP) separately and western blot experiments were conducted independently for E-cadherin, CD44, vimentin and NF-KB p65. PKC-ζ IP samples did not show any association with any mentioned proteins. Only vimentin western blot showed a band for PKC-ι IP samples (FIG. 13A). This result suggests that PKC-ι associate with vimentin. To confirm this association, vimentin was immunoprecipitated and developed for said proteins (FIG. 9B) and only PKC-ι produced a band.

EXAMPLE 26: Specific Binding of ζ-Stat to PKC-ζ

Figure 14A:
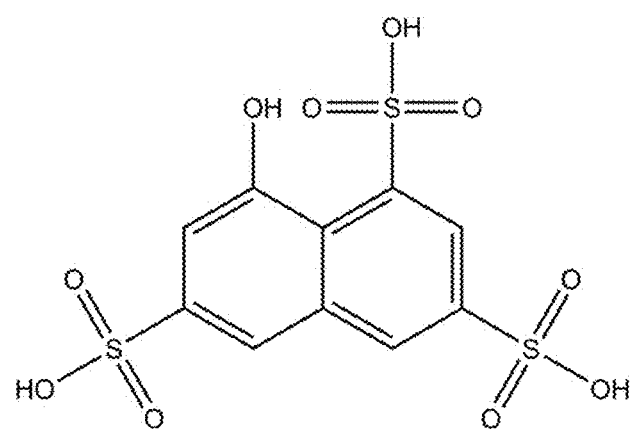
FIG. 14A shows the chemical structures of ζ-Stat.
Figure 14B:
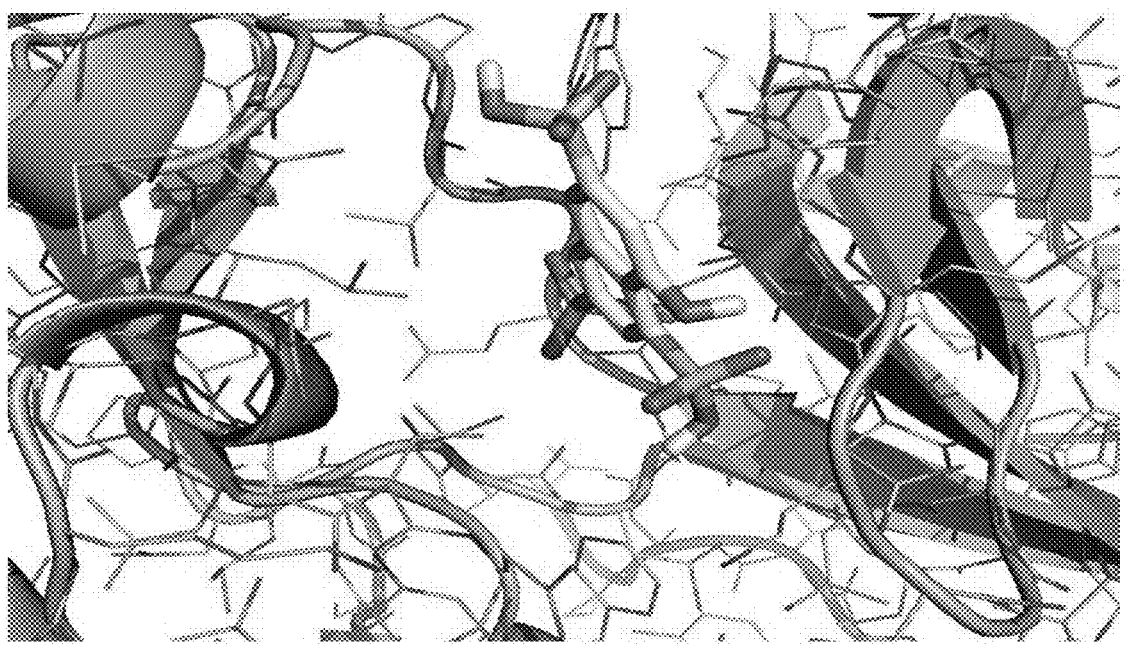
FIG. 14B shows the molecular docking (MD) of ζ-Stat on PKC-ζ.

The chemical structure of ζ-Stat and the molecular docking (MD) of ζ-Stat on PKC-ζ are shown in FIGS. 14A and 14B. Molecular weight of ζ-Stat is 384.34 g/mol. ζ-Stat interacts with amino acid residues of 251-547 (I251, R253, V259, K274, D544, and F547) of the catalytic domain of PKC-ζ. ζ-Stat is specific only to PKC-ζ.

EXAMPLE 27: Effects of ζ-Stat on Malignant Cells

Figure 15A:
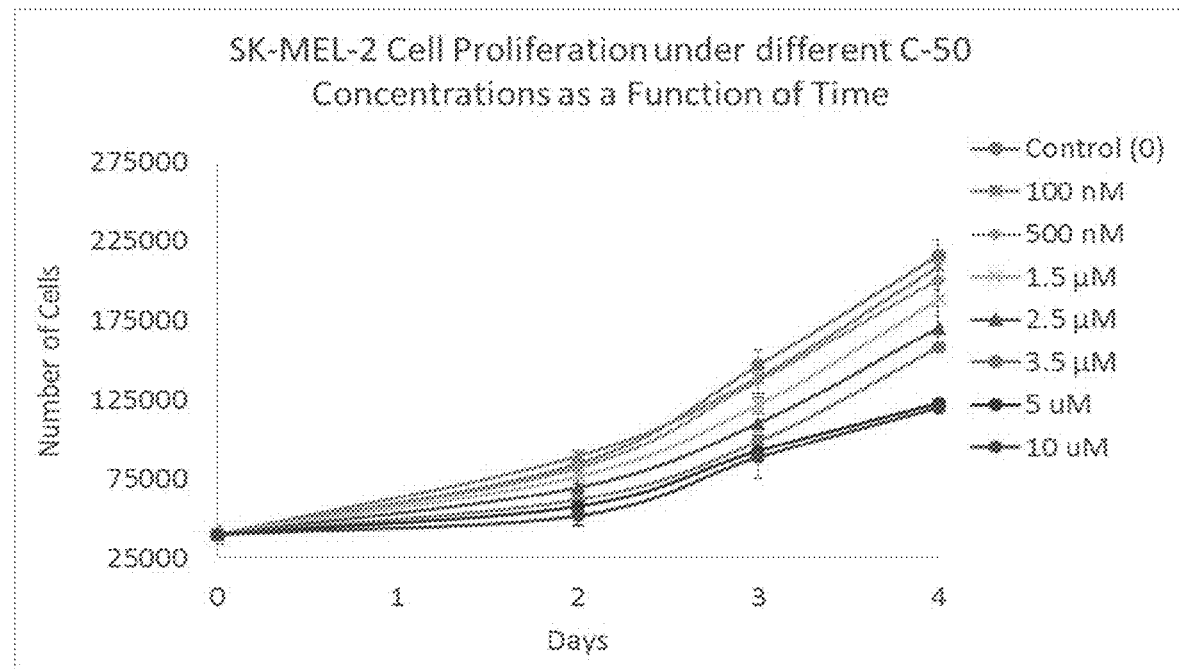
FIG. 15A shows the effects of ζ-Stat on SK-MEL-2 cell numbers.
Figure 15B:
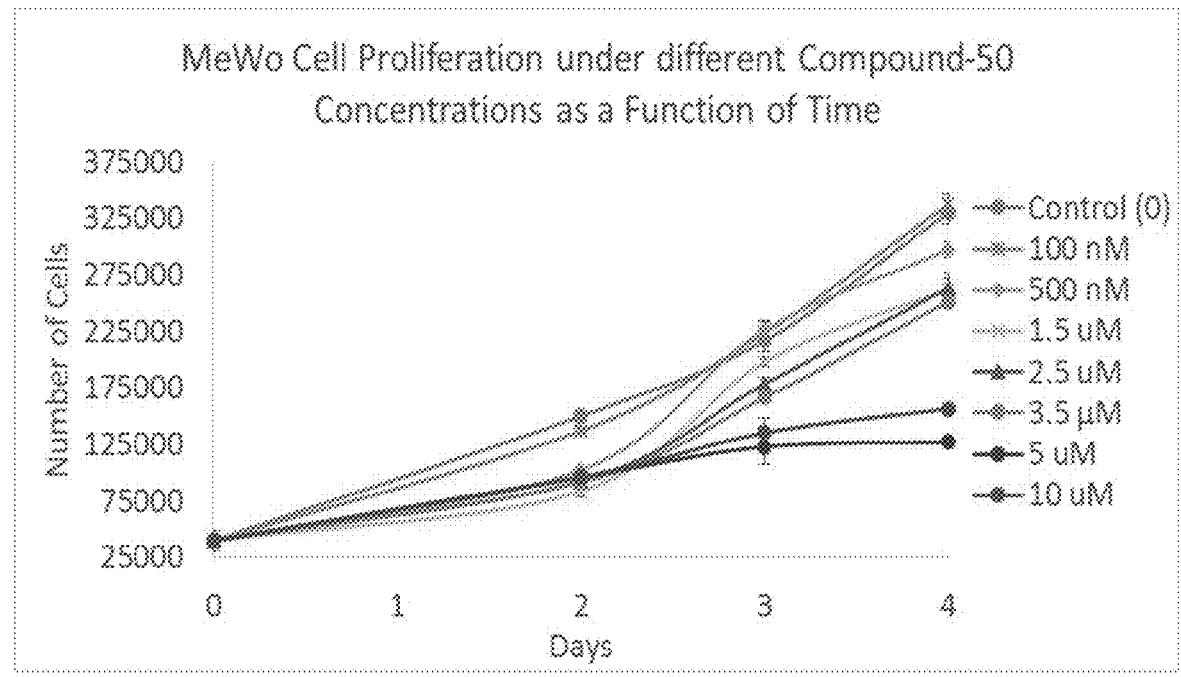
FIG. 15B shows the effects of ζ-Stat on MeWo cell numbers.

To test the effects of ζ-Stat on malignant cells approximately $4 \times 10^4$ of cells were cultured in 25 cm2 flasks and treated with either equal volume of sterile water (control) or ζ-Stat (0.1-10 μM). Additional doses of sterile water or inhibitor were supplied every 24 h during 3 day incubation period. Subsequently, cells were lifted and counted. Cells were quantified by counting the viable cells at 24 hour intervals. The results showed the effect of ζ-Stat on SK-MEL-2 (FIG. 15A) and on MeWo (FIG. 15B). N=3 experiments were performed for each cell line and mean±SD are plotted.

Figure 16A:
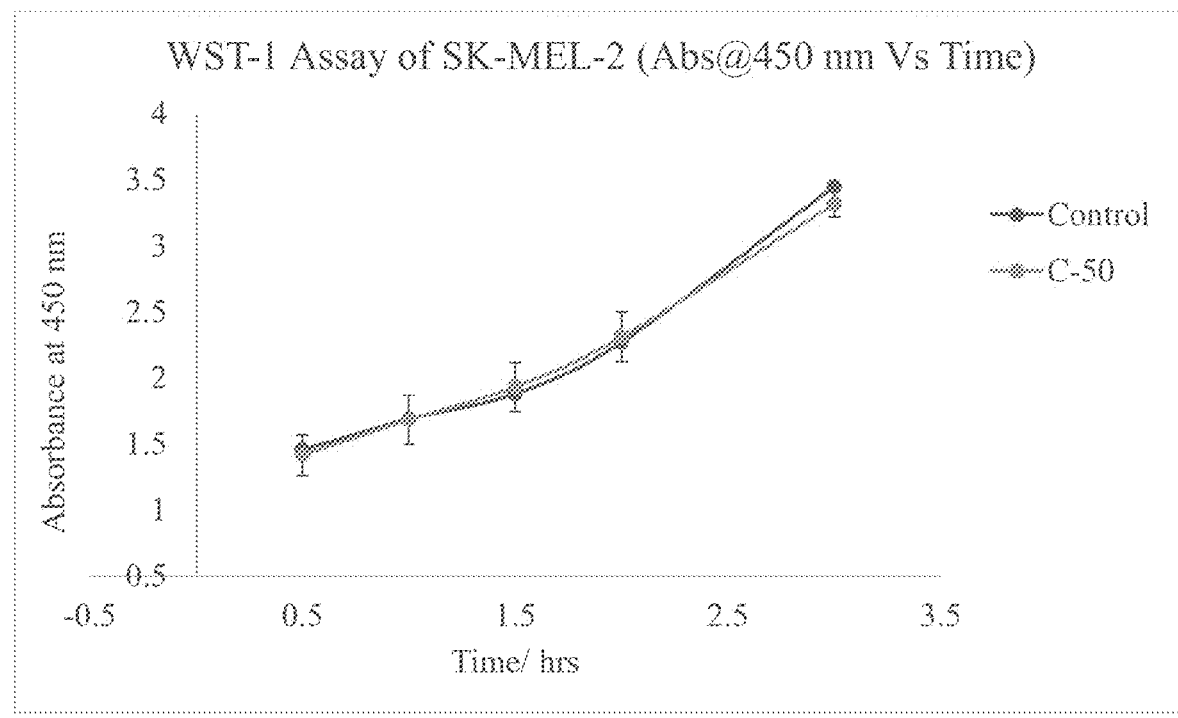
FIG. 16A shows the effect of ζ-Stat on cell proliferation using the WST-1 assay for PCS-200-013 cells.
Figure 16B:
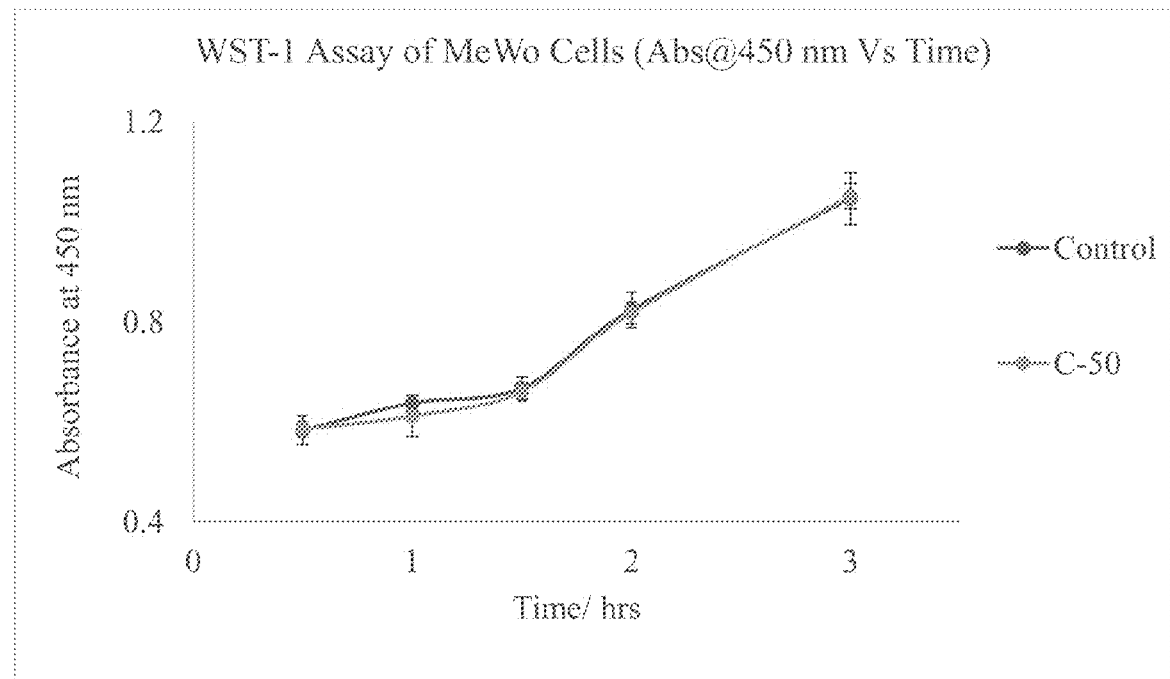
FIG. 16B shows the effect of ζ-Stat on cell proliferation using the WST-1 assay for SK-MEL-2 cells.

EXAMPLE 28: Effects of ζ-Stat from WST-1 Assay for Cell Viability and Cytotoxicity Cell proliferation was measured using WST-1 assay for SK-MEL-2 (FIG. 16A) and MeWo (FIG. 16b). Absorbance at 450 nm due to production of water soluble formazan was measured as a function of time and the absorbance is directly proportional to the number of cells. The experimental concentration for ζ-Stat was 2.5 μM. N=3 experiments were performed for each cell line and mean±SD are plotted.

Figure 17A:
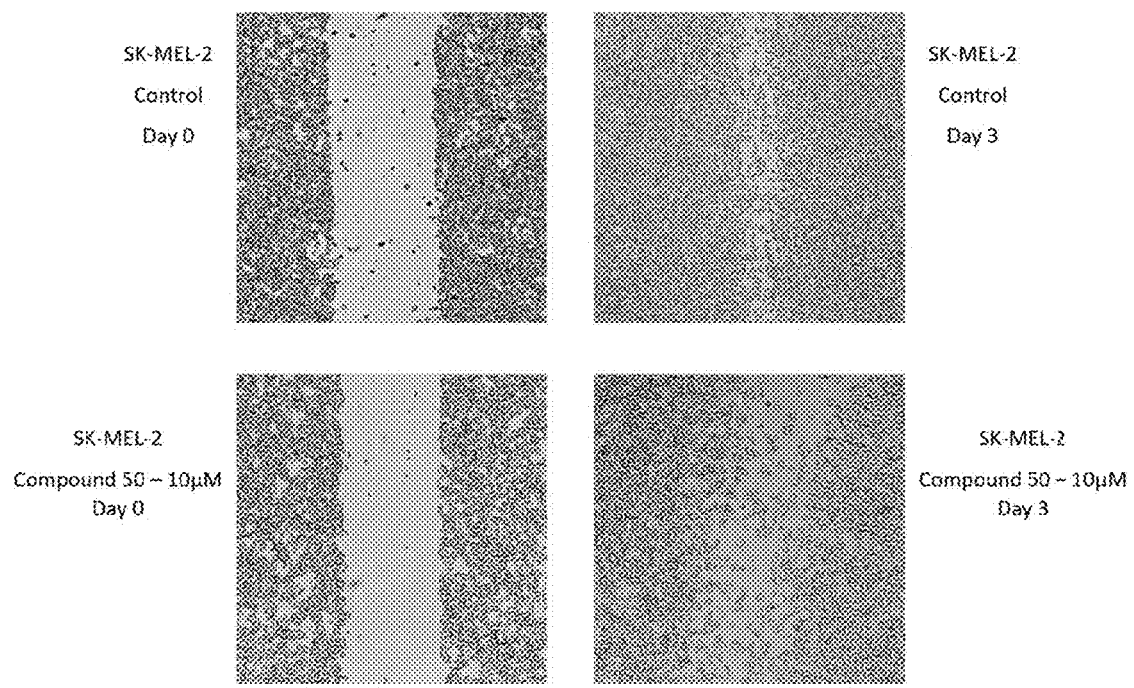
FIG. 17A shows melanoma cell migration measured using a wound healing assay for SK-MEL-2 cells in the absence and presence of ζ-Stat.
Figure 17B:
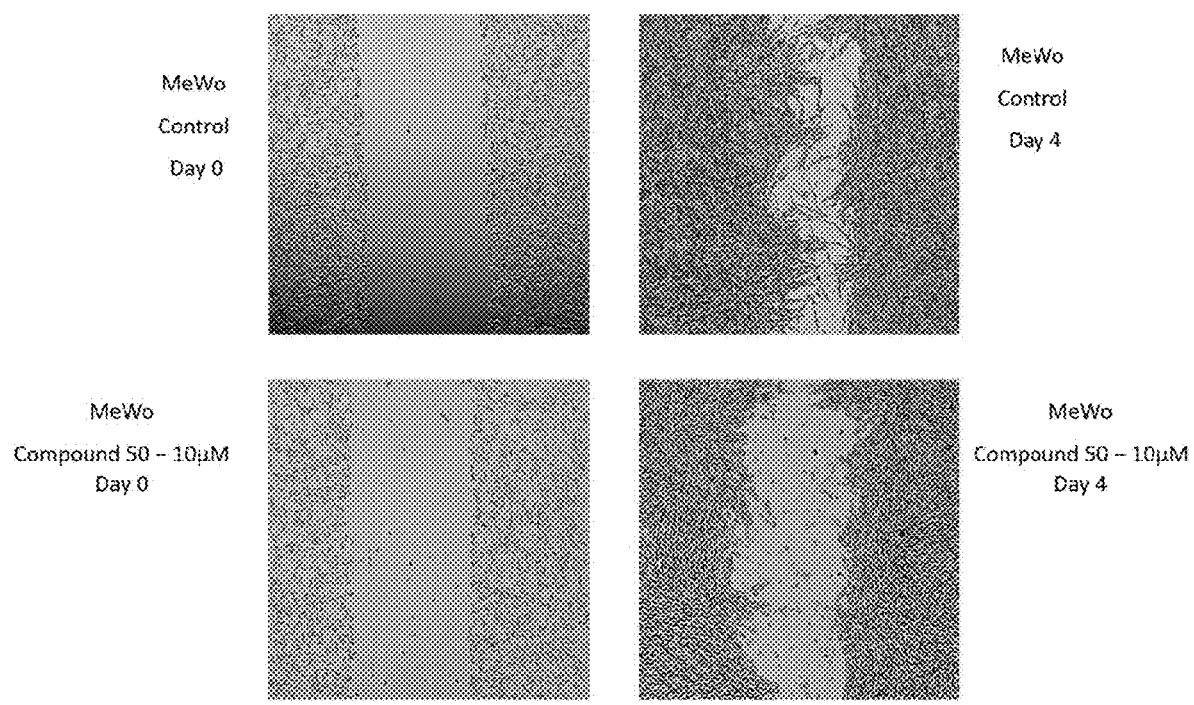
FIG. 17B shows melanoma cell migration measured using a wound healing assay for MeWo cells in the absence and presence of ζ-Stat. a wound healing assay pictures of ACPD treated SK-MEL-2 cells.

EXAMPLE 29: Effects of ζ-Stat on Melanoma Cell Migration Using Wound Healing Assay Microscopic photographs of scratches on cells at the beginning (day 0) were compared with the photographs taken after 3 or 4 days the effects of inhibitors are shown for SK-MEL-2 (FIG. 17A) compared to its control. A1 and A2 for control, A3 and A4 for ζ-Stat 10 μM. Effect of ζ-Stat shown for MeWo (FIG. 17B) compared to its control. B1 and B2 for control, B3 and B4 for Compound-50 10 μM. N=3 experiments were performed for each cell line and randomly picked photographs are shown.

EXAMPLE 30: Effects of Inhibitors on Expression of aPKC as Determined by Western Blots The change of levels of phosphorylated PKC-ι, total PKC-ι (FIG. 18A) and change of levels of phosphorylated PKC-ζ, total PKC-ζ (FIG. 18B) are shown for the ζ-Stat treated (2.5 μM) samples of malignant melanoma cell lines (SK-MEL-2 and MeWo) after the end of 3rd day of treatments. β-actin was used as the internal loading control in each Western blot. Whole cell lysate of 40 μg was separated on 7.5% SDS-PAGE and the Western blots of above proteins were obtained. N=3 experiments were performed in each case.

Based on these results, ζ-Stat can effectively reduce the malignancy of melanoma cell lines in vitro. Molecular docking confirmed that ζ-Stat specifically binds to PKC-ζ and results of kinase activity assay show more than 50% of inhibition of PKM-ζ activity (a homologous of PKC-ζ found in human brain) but it does not effect on PKC-ι. PKC-ζ acts as a pro-growth protein in many human cancer cells/tissues. Therefore, effective inhibition can lead to cure malignant tumors based on specific markers. According to the WST-1 assay, ζ-Stat did not show toxicity to malignant melanoma cells at the tested concentration (2.5 μM) which had only 20-25% inhibition of cell viability according to the cell counts on viability. But 5 μM and 10 μM concentrations produced an inhibition close to 50% hence future tests will be performed using 7-7.5 μM of ζ-Stat. At the tested concentration, the protein levels of total PKC-ι and phosphorylated PKC-ι levels did not change significantly but total PKC-ζ level was reduced by 42% and the pPKC-ζ level reduced by 37%. Additionally, we found that ζ-Stat plays a role in altering the levels of proteins which are used as epithelial to mesenchymal transition (EMT). We also found that treatment of ζ-Stat (C-50) induces the apoptosis of malignant melanoma cells.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

REFERENCES

[1] National Cancer Institute: PDQ® Melanoma Treatment. Bethesda, Md.: National Cancer Institute. Date last modified <Feb. 2, 2016>. See, world-wide website: cancer.gov/types/skin/hp/melanoma-treatment-pdq.

[2] Lens, M. B., Dawes, M. (2004)"Global perspectives of contemporary epidemiological trends of cutaneous malignant melanoma" *Brit. J. Dermatol.;* 150: 179-185.

[3] NIH Surveillance, Epidemiology and End Results (SEER) program report (see world-wide web site: cancer.gov/statistics/types/survival.html)

[4] Lee, J., Strickland, D., (1980). "Malignant melanoma: social status and outdoor work". *Brit. J. Cancer;* 41(5): 757-63.

[5] Pollock, P. M., Meltzer, P. S., (2002) "A genome-based strategy uncovers frequent BRAF mutations in melanoma" *Cancer Cell;* 2(1): 5-7.

[6] Cutler, R. E., Stephens, R. M., Saracino, M. R., Morrison, D. K., (1998). "Autoregulation of the Raf-1 serine/threonine kinase". *P. Natl. Acad. Sci. USA;* 95(16): 9214-9219.

[7] Greene, M. H., (1998). "The genetics of hereditary melanoma and nevi". *Cancer;* 86(11): 2464-2477.

[8] Halachmi, S., Gilchrest, B. A., (2001). "Update on genetic events in the pathogenesis of melanoma". *Curr. Opin. Oncol.;* 13(2): 129-136.

[9] Manning, G., et al. (2002). "The protein kinase complement of the human genome". *Science;* 298(5600): 1912-1934.

[10] Kishimoto, A., et al. (1980). "Activation of calcium and phospholipid-dependent protein kinase by diacylglycerol, its possible relation to phosphatidylinositol turnover". *J. Biol. Chem.;* 255: 2273-2276.

[11] Castagna, M., et. al. (1982). "Direct activation of calcium-activated, phospholipid-dependent protein kinase by tumor-promoting phorbol esters". *J. Biol. Chem.;* 257: 7847-7851.

[12] Wilson, C. H., et. al. (2015). "Steatosis inhibits liver cell store-operated $Ca^{2+}$ entry and reduces ER $Ca^{2+}$ through a protein kinase C-dependent mechanism". *Biochem. J.;* 466 (2): 379-390.

[13] Mellor, H., (1998). "The extended protein kinase C superfamily". *Biochem. J.;* 332 (2): 281-292.

[14] Selzer, et. al. (2002) "Protein kinase C isoforms in normal and transformed cells of the melanocytic lineage". Melanoma Res.; 12: 201-209.

[15] Jim Woodgett, Protein Kinase Function, 2$^{nd}$ edition, Oxford University Press, (2000), 13-22.

[16] Regala, R. P., Weems, C., Jamieson, L., Copland, J. A., Thomson, E. A., Fields, A. P., (2005) "Atypical protein kinase C iota plays a role in human lung cancer cell growth and tumorigenicity". *J. Biol. Chem.;* 180: 31109-31115.

[17] Bandyopadhyay, G., Sajan, M. P., Kanoh, Y., Standaert, M. L., Quon, M. J., Lea-Currie, R., Sen, A., Farese, R. V., (2002). "PKC-zeta mediates insulin effects on glucose transport in cultured preadipocyte-derived human adipocytes". *J. Clin. Endocr. Metab.;* 87(2): 716-723.

[18] Plant, P. J., Fawcett, J. P., Lin, D. C., Holdorf, A. D., Binns, K., Kulkarni, S., Pawson, T. A., (2003) "polarity complex of mPar-6 and atypical PKC binds, phosphorylates and regulates mammalian Lgl". *Nat. Cell Biol.;* 5(4): 301-308.

[19] Regela, R. P., Weems, C., Jamieson, L., et. al. (2005) "Atypical protein kinase C iota is an oncogene in human non-small cell lung cancer". *Cancer Res.;* 65: 8905-8911.

[20] Selzer, et. al. (2002) "Protein kinase C isoforms in normal and transformed cells of the melanocytic lineage". *Melanoma Res.;* 12: 201-209.

[21] Murray, N. R., Fields, A. P., (1997) "Atypical protein kinase C iota protects human leukemia cells against drug induced apoptosis". *J. Biol. Chem.;* 272: 27521-27524.

[22] Acevedo-Duncan, M., Patel, R., Whelan, S., Bicaku, E., (2002) "Human glioma PKC-ι and PKC-βII phosphorylate cyclin dependent kinase activating kinase during the cell cycle". *Cell Proliferat.;* 35: 23-26.

[23] Patel, R., Win, H., Desai, S., Patel, K., Matthews, J. A., Acevedo-Duncan, M., (2008) Involvement of PKC-ι in cell proliferation. *Cell Proliferat.;* 41: 122-135.

[24] Dissanayake, S. K., Wade, M., Johnson, C. E., O'Connell, M. P., Leotlela, P. D., French, A. D., Shah, K. V., Hewitt, K. J., Rosenthal, D. T., Indig, F. E., Jiang, Y., Nickoloff, B. J., Taub, D. D., Trent, J. M., Moon, R. T., Bittner, M., Weeraratna, A., (2007) "The Wnt5A/Protein Kinase C Pathway Mediates Motility in Melanoma Cells via the Inhibition of Metastasis Suppressors and Initiation of an Epithelial to Mesenchymal Transition", *J. Biol. Chem.;* 282(23): 17259-17271.

[25] Weeraratna, A., Jiang, Y., Hostetter, G., Rosenblatt, K., Duray, P., Bittner, M., Trent, J. M., (2002) "Wnt5a signaling directly affects cell motility and invasion of metastatic melanoma". *Cancer Cell;* 1:279-288.

[26] World-wide website: home.ccr.cancer.gov/connections/2011/Vol5_No1/clinic.asp

[27] Takanori, S., Croft, M., (2012) "Regulation of the PKCθ-NF-κB axis in T lymphocytes by the tumor necrosis factor receptor family member OX40". *Front. Immunol.;* 3(133): 1-8.

[28] Shao-Cong, S. (2011)"Non-canonical NF-κB signaling pathway". *Cell Res.;* 21: 71-85.

[29] Liu, N., Sun, Q., Chen, J., Li, J., Zeng, Y., Zhai, S., Li, P., Wang, B., Wang, X., (2012) "MicroRNA-9 suppresses uveal melanoma cell migration and invasion through the NF-κB1 pathway", *Oncol. Rep.;* 28: 961-968.

[30] Semenov, M., Bryan, R. H., MacDonald, T., He, X., (2007) "SnapShot: Noncanonical Wnt Signaling Pathways", *Cell;* 131, 1378.

[31] O'Connell, M. P., Fiori, J. L., Xu, M., Carter, A. D., Frank, B. P., Camilli, T. C., French, A. D., Dissanayake, S. K., Indig, F. E., Bernier, M., Taub, Hewitt, S. M., Weeraratna, A. T., (2010) "The Orphan Tyrosine Kinase Receptor, ROR2, Mediates Wnt5A Signaling in Metastatic Melanoma". *Oncogene;* 29(1): 34-44.

[32] Vultur, A., Villanueva, J., Krepler, C., Rajan, G., Chen, Q., Xiao, M., Li, L., Gimotty, P. A., Wilson, M., Hayden, J., Keeney, F., Nathanson, K. L., Herlyn, M., (2-14) "MEK inhibition affects STAT3 signaling and invasion in human melanoma cell lines". *Oncogene;* 33: 1850-1861.

[33] McKinsey, T. A., Kass, D. A, (2007) "Small-molecule therapies for cardiac hypertrophy: moving beneath the cell surface". *Nature Rev. Drug Discov.;* 6: 617-635.

[34] Hideji, M., Hong, W., Ryohei, Y., (2011) "Local, persistent activation of Rho GTPases during plasticity of single dendritic spines". *Nature;* 472(7341): 100-104.

[35] Pillai, P. et al. (2011)

[36] Guertin, M. J., Petesch, S. J., Zobeck, K. L., Min, I. M., Lis, J. T., (2010) "*Drosophila* heat shock system as a general model to investigate transcriptional regulation". *Cold Spring Harb Symp Quant. Biol;* 75: 1-9.

[37] Salamanca, H. H., Fuda, N., Shi, H., Lis, J. T., (2011). "An RNA aptamer perturbs heat shock transcription factor activity in *Drosophila melanogaster*". *Nucleic Acids Res;* 39(15): 6729-6740.

We claim:

1. A method of treating a melanoma in a subject in need thereof, the method comprising administering to the subject a therapeutically effective amount of an inhibitor of an atypical protein kinase C (aPKC),
  wherein the aPKC inhibitor is 2-acetyl-1,3-cyclopentanedione (ACPD).

2. The method of claim 1, wherein the aPKC is PKC-zeta.

3. A method of inhibiting a melanocyte proliferation, the method comprising contacting the melanocyte with a therapeutically effective amount of an inhibitor of an aPKC, whereby melanocyte proliferation is inhibited,
  wherein the aPKC inhibitor is ACPD.

4. The method of claim 3, wherein the aPKC is PKC-zeta.

5. A method of reducing levels of at least one aPKC in a cell, the method comprising contacting the cell with a therapeutically effective amount of an inhibitor of an aPKC, whereby the level of at least one aPKC in the cell is reduced,
  wherein the aPKC inhibitor is ACPD.

6. The method of claim 5, wherein the cell is a melanocyte cell.

7. The method of claim 5, wherein the aPKC is PKC-zeta.

8. A method of inhibiting aPKC in a cell, the method comprising contacting the cell with a therapeutically effective amount of an inhibitor of an aPKC, wherein the aPKC inhibitor is ACPD, DNDA, or ζ-stat.

9. The method of claim 8, wherein the cell is a melanoma cell.

* * * * *